US010299952B2

(12) United States Patent
Nordt, III et al.

(10) Patent No.: US 10,299,952 B2
(45) Date of Patent: May 28, 2019

(54) SUPPORTS INCLUDING DUAL PIVOT AXES FOR HINGE JOINT

(75) Inventors: William E. Nordt, III, Charles City, VA (US); Ian D. Kovacevich, Charlotte, NC (US); Jason Huneycutt, Charlotte, NC (US); Thomas J. Philpott, Charlotte, NC (US)

(73) Assignee: NORDT DEVELOPMENT CO., LLC, Charles City, VA (US)

( * ) Notice: Subject to any disclaimer, the term of this patent is extended or adjusted under 35 U.S.C. 154(b) by 1036 days.

(21) Appl. No.: 13/241,865

(22) Filed: Sep. 23, 2011

(65) Prior Publication Data
US 2012/0016284 A1 Jan. 19, 2012

Related U.S. Application Data

(63) Continuation of application No. 12/101,763, filed on Apr. 11, 2008, now abandoned.

(51) Int. Cl.
*A61F 5/01* (2006.01)

(52) U.S. Cl.
CPC ............ *A61F 5/0102* (2013.01); *A61F 5/013* (2013.01); *A61F 5/0123* (2013.01); *A61F 2005/0137* (2013.01); *A61F 2005/0172* (2013.01)

(58) Field of Classification Search
USPC ...... 602/5, 6, 14, 16, 20, 21, 23, 26, 60–62, 602/75; 128/846, 869, 878, 881, 882
See application file for complete search history.

(56) References Cited

U.S. PATENT DOCUMENTS

| 1,466,487 A | 8/1923 | Shaffer |
| 5,662,595 A | 9/1997 | Chesher et al. |
| 5,916,186 A | 6/1999 | Turto et al. |
| 7,118,543 B2 | 10/2006 | Telles et al. |
| 7,156,819 B2 | 1/2007 | Sieller et al. |
| 7,490,458 B2 | 2/2009 | Ford |
| 7,878,998 B2 | 2/2011 | Nordt et al. |
| 7,887,500 B2 | 2/2011 | Nordt et al. |

(Continued)

FOREIGN PATENT DOCUMENTS

| RE | 30501 | 2/1981 |
| WO | 9106265 | 5/1991 |
| WO | 9310727 | 6/1993 |

OTHER PUBLICATIONS

Information Disclosure Statement (IDS) Letter Regarding Common Patent Application(s), dated Jan. 30, 2013.

*Primary Examiner* — Kari K Rodriquez
(74) *Attorney, Agent, or Firm* — Chad D Tillman; Jeremy C Doerre; Tillman Wright, PLLC

(57) ABSTRACT

A support for an area of a body having a hinge joint includes: a flexible, elastically stretchable framework configured to extend across the hinge joint of the area of the body; and a hinge mechanism affixed to the framework. The hinge mechanism includes a strut component and a first arm component connected to the strut component such that the first arm component is rotatable relative to the strut component only about a first pivot axis. A second arm component is connected to the strut component such that the second arm component is rotatable relative to the strut component only about a second pivot axis. The strut component is configured to extend with the framework across the hinge joint such that the first pivot axis is located on a first side of the hinge joint and the second pivot axis is located on a second, opposite side of the hinge joint.

20 Claims, 47 Drawing Sheets

(56) References Cited

U.S. PATENT DOCUMENTS

| | | |
|---|---|---|
| 7,922,680 B2 | 4/2011 | Nordt et al. |
| 7,993,296 B2 | 8/2011 | Nordt et al. |
| 8,162,867 B2 | 4/2012 | Nordt et al. |
| 2005/0054960 A1 | 3/2005 | Telles et al. |
| 2009/0259156 A1 | 10/2009 | Nordt et al. |
| 2010/0331748 A1 | 12/2010 | Nordt et al. |
| 2012/0245499 A1 | 9/2012 | Nordt et al. |

402

| ITEM NO. | PART NUMBER | DESCRIPTION | QTY. |
|---|---|---|---|
| 1 | KNEE BRACE WEB | CO-INJECTION MOLDED TPE | 1 |
| 2 | HINGE STAY ANCHOR | NYLON, BLACK (CO-MOLDED) | 2 |
| 3 | UPPER STAY ANCHOR | NYLON, BLACK (CO-MOLDED) | 2 |
| 4 | LOWER STAY ANCHOR | NYLON, BLACK (CO-MOLDED) | 2 |
| 5 | HINGE STAY MEMBER CALF | NYLON, BLACK (RIVETED) | 2 |
| 6 | HINGE STAY MEMBER THIGH | NYLON, BLACK (RIVETED) | 2 |

402

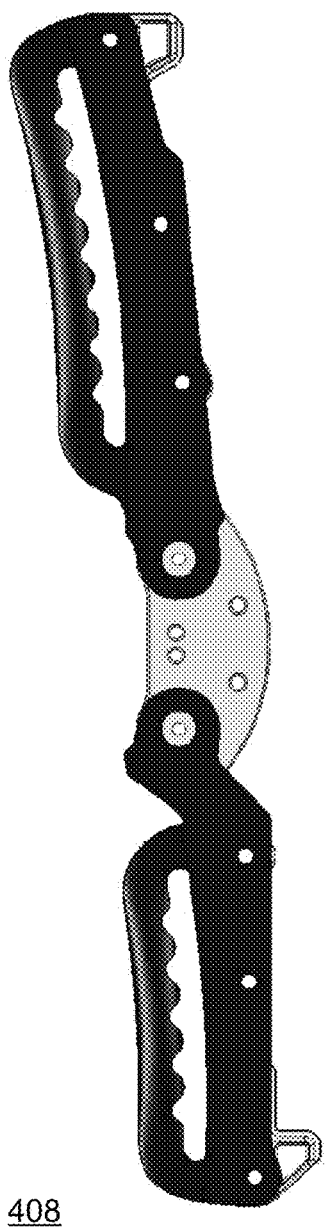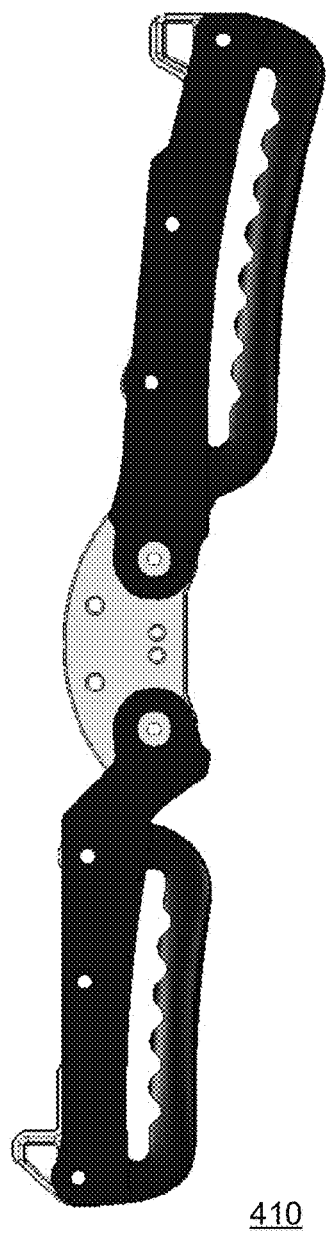
408    FIG. 33a    410

410          408

SUPPORTS INCLUDING DUAL PIVOT AXES FOR HINGE JOINT

CROSS-REFERENCE TO RELATED APPLICATION

The present application is a U.S. continuation patent application of, and claims priority under 35 U.S.C. § 120 to, U.S. nonprovisional patent application Ser. No. 12/101,763, filed Apr. 11, 2008, which nonprovisional patent application published as U.S. patent application publication no. 2009/0259156 A1, which patent application and any patent application publications thereof are hereby incorporated by reference herein.

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE INVENTION

Joint fatigue, pain, and instability are common conditions of active and aging people. This is especially true with regard to hinge joints of the body, including the knee joint and the elbow joint. Such joint ailments often can be attributed to damage to, and degenerative wear in, the contact surfaces of bone ends meeting at the joint. External support in these areas of the body can help address joint fatigue, pain, and/or instability and, generally, external support in various areas of the body can serve to address many different conditions. One or more aspects of the invention provide such support. Moreover, one or more aspects of the invention even augment motion about joints and, in particular, about hinge joints.

Additionally, several embodiments of improved supports that address the foregoing concerns are disclosed in the following U.S. patent application publications, each of which is hereby incorporated herein by reference: US 2008-0065230 A1; US 2008-0039757 A1; US 2008-0039766 A1; US 2006-0030804 A1; US 2006-0030805 A1; US 2006-0030806 A1; US 2006-0026733 A1; US 2006-0026736 A1; US 2006-0070165 A1; US 2006-0070164 A1; US 2006-0026732 A1; US 2006-0030803 A1; and US 2006-0030802 A1.

Supports in accordance with embodiments of the present application represent yet further such supports that address the foregoing concerns.

SUMMARY OF THE INVENTION

The invention relates to various supports for the body and, with respect to certain embodiments, the invention relates to potentiating supports for hinge joints of the body. Indeed, certain supports are designed for the area of the knee and other supports are designed for the area of the elbow. Other supports of the present invention include clothing having expandable and recoverable frameworks for support of areas of the body. These supports of the invention are useful for injury treatment or prevention, rehabilitation, and motion enhancement.

For example, a preferred potentiating support for the knee provides a secure fitting and comfortable knee brace for the purposes of supporting knee alignment, comfort, and protection in the activities of daily living, athletics, and working and in the treatment or rehabilitation of an injured or ailing knee, all the while providing joint motion assistance for performance enhancement in everyday and athletic activities. In this regard, kinetic energy is stored and returned for use to assist the body in its natural knee movement in a preferred knee support of the present invention. Embodiments of these supports, as well as aspects and features of the invention, are set forth below and in the detailed description section herein.

Accordingly, in an aspect of the invention, a support for an area of a body having a hinge joint includes: a flexible, elastically stretchable framework configured to extend across the hinge joint of the area of the body; and a hinge mechanism affixed to the framework, the hinge mechanism comprising a strut component and first and second arm components. The first arm component is connected to the strut component such that the first arm component is rotatable relative to the strut component only about a first pivot axis; the second arm component is connected to the strut component such that the second arm component is rotatable relative to the strut component only about a second pivot axis; and the strut component is configured to extend with the framework across the hinge joint such that the first pivot axis is located on a first side of the hinge joint and the second pivot axis is located on a second, opposite side of the hinge joint.

In a feature of this aspect, the flexible framework comprises an elastomeric material.

In a feature of this aspect, the flexible framework is configured to be stretched and tensioned into abutment with the area of the body such that the flexible framework conforms to the shape and contour of the area of the body when stretched and tensioned, the flexible framework having a relaxed state when not stretched and tensioned in which the flexible framework does not conform to the shape and contour of the area of the body.

In a feature of this aspect, the framework is in a first configuration when the hinge mechanism is in a first position, and the framework is in a second configuration when the hinge mechanism is in a second position, the elastically stretchable framework storing potential energy that is released as kinetic energy upon transitioning of the hinge mechanism from the second position to the first position.

In a feature of this aspect, the framework defines a flexible, elastically stretchable web of elastomeric interconnecting members.

In a feature of this aspect, the strut component is at least partially embedded in a material of the framework.

In a feature of this aspect, the framework encompasses and completely encircles at least a middle portion of the strut component.

In a feature of this aspect, each of the first and second arm components is at least partially embedded in a material of the framework.

In a feature of this aspect, a first hinging member connects the first arm component to the strut component, the first hinging member including a cylindrical portion in abutment with which the first arm component and strut component rotate, and wherein a second hinging member connects the second arm component to the strut component, the second hinging member including a cylindrical portion in abutment with which the second arm component and strut component rotate, the first axis extending through the cylindrical portion of the first hinging member and the second axis extending through the cylindrical portion of the second hinging member.

In a feature of this aspect, the support further includes first and second strap interface components, each strap interface component being affixed to the framework, the first strap interface component being connected to the first arm component and defining at least one opening therein configured to receive therethrough a strap for attachment of the framework to the body on the first side of the hinge joint, and the second strap interface component being connected to the second arm component and defining at least one opening therein configured to receive therethrough a strap for attachment of the framework to the body on the second side of the hinge joint.

In a feature of this aspect, each of the first and second strap interface components are at least partially embedded in a material of the framework.

In a feature of this aspect, the hinge mechanism is located along a first side edge of the framework, and the support further comprises a second, identical hinge mechanism affixed to the framework and located along a second, opposite side edge of the framework, the strut component of the second hinge mechanism being configured to extend with the framework across the hinge joint such that the first pivot axis of the second hinge mechanism is located on the first side of the hinge joint and the second pivot axis of the second hinge mechanism is located on the second side of the hinge joint.

In accordance with another aspect of the invention, a support for an area of a body having a hinge joint includes: (a) a flexible, elastically stretchable framework comprising a web of elastomeric interconnecting members, the web including an intermediate portion configured to extend across the hinge joint; (b) a first hinge mechanism affixed to the web proximate a first side of the intermediate portion of the web, the first hinge mechanism comprising a strut component at least partially embedded in a material of the web and first and second arm components at least partially embedded in the material of the web, the first and second arm components being connected to respective opposite end portions of the strut component such that the first and second arm components are rotatable relative to the strut component about respective pivot axes located at opposite end portions of the strut component; and (c) a second hinge mechanism affixed to the web proximate a second, opposite side of the intermediate portion of the web, the second hinge mechanism comprising a strut component at least partially embedded in the material of the web and first and second arm components at least partially embedded in the material of the web, the first and second arm components of the second hinge mechanism being connected to respective opposite end portions of the strut component of the second hinge mechanism such that the first and second arm components of the second hinge mechanism are rotatable relative to the strut component of the second hinge mechanism about respective pivot axes located at opposite end portions of the strut component of the second hinge mechanism. In accordance with this aspect, each of the strut components and arm components of the first and second hinge mechanisms comprises components that are distinct from one another.

In a feature of this aspect, the web encompasses and completely encircles at least a middle portion of the strut component.

In another feature of this aspect, the support further includes strap interface components, with each strap interface component being affixed to the web. Specifically, the first strap interface component is connected to the first arm component and defines at least one opening therein configured to receive therethrough a strap for attachment of the web to the body on a first side of the hinge joint, and the second strap interface component is connected to the second arm component and defines at least one opening therein configured to receive therethrough a strap for attachment of the web to the body on the second side of the hinge joint.

In a feature of this aspect, each of the strap interface components is at least partially embedded in the material of the web.

In a feature of this aspect, each of the strut components and arm components of the first and second hinge mechanisms comprises a generally planar component.

In accordance with another aspect of the invention, a method for supporting an area of a body that has a hinge joint includes providing a support comprising: (i) a flexible framework configured to extend across the hinge joint of the area of the body, the flexible framework comprising an elastically stretchable material; (ii) a first hinge mechanism affixed to the framework; and (iii) a second hinge mechanism affixed to the framework. The first hinge mechanism itself includes first, second and third distinct components, with the first and second components being connected together such that the first and second components are rotatable relative to each other about a first pivot axis, and with the second and third components being connected together such that the second and third components are rotatable relative to each other about a second pivot axis. Similarly, the second hinge mechanism includes first, second and third distinct components, with the first and second components of the second hinge mechanism being connected together such that the first and second components of the second hinge mechanism are rotatable relative to each other only about a first pivot axis of the second hinge mechanism, and with the second and third components of the second hinge mechanism being connected together such that the second and third components of the second hinge mechanism are rotatable relative to each other only about a second pivot axis of the second hinge mechanism.

The method further includes positioning the support against the body such that: (i) the support extends across the hinge joint and such that the second components of the first and second hinge mechanisms extend with the framework across the hinge joint of the body, with the first pivot axes of the first and second hinge mechanisms being located on a first side of the hinge joint of the body and the second pivot axes of the first and second hinge mechanisms being located on a second, opposite side of the hinge joint of the body; and (ii) the second components of the first and second hinge mechanisms extend on opposite sides of the hinge joint of the body.

In a feature of this aspect, the area of the body comprises an area of the knee, and the support extends across the knee such that the second components of the first and second hinge mechanisms extend across the knee, with the first pivot axes of the first and second hinge mechanisms being located above the knee and the second pivot axes of the first and second hinge mechanisms being located below the knee.

In a feature of this aspect, the step of positioning the support includes tensioning the framework in abutment with the area of the body—including the hinge joint—and fastening the support to the body on opposite sides of the hinge joint of the body such that the framework is held in tension in its abutment with the area of the body. In so doing, the elastically stretchable framework conforms to the surface contour of the area of the body as a result of said tensioning.

Additionally, in accordance with these and other aspects and features of the invention, many of the inventive supports each includes a framework having a surface for abutment with an area of a body. The framework extends in generally first and second directions to define a surface of the framework for abutment with the area of the body. With reference to a cylindrical coordinate system, the framework of the support generally extends in a first axial direction and may extend in a second circumferential direction to define the surface of the framework, which is intended to abut an area of the body when the support is worn, such as a portion of an arm, leg, or torso. Because the framework extends in axial and circumferential directions, the surface of the framework generally is shaped to fit an area of a leg, arm, or torso in its abutting engagement with the body. Furthermore, in many preferred embodiments, the support spans and supports an area that includes a hinge joint of the body and, in such embodiments, the support comprises a potentiating support for the hinge joint. As used herein, a "hinge joint" refers to a knee joint or an elbow joint and is characterized in that the joint provides hinging movement that is generally limited to being within a plane.

In further accordance with these and other aspects and features of the invention, the framework is formed from one or more elastomeric materials such that the framework is expandable and recoverable. As used herein, "elastomeric material" refers to "a material that is capable of being easily expanded and resuming former shape." Something that has the ability to resume its former shape after expansion or compression is referred to herein as being "recoverable." Something that is expandable and recoverable also is referred to herein as being "elastically stretchable." This is in contrast to something that is "resilient," which refers to having "the ability to resume its former shape after compression." Preferably, the framework also is flexible (i.e., pliable) and is capable of conforming to the general area of the body to be supported without substantial stretching; however, it is contemplated within the invention that the framework may need to be stretched to a certain extent in order for the surface of the framework to conform to the general area of the body to be supported. As used herein, "flexible" refers to "the ability to bend freely and repeatedly without breaking."

Still in accordance with these and other aspects and features of the invention, the framework defines at least one permanent opening in a surface thereof regardless of whether the support is donned and regardless of whether the surface of the framework is in abutment with the area of the body to be supported. The at least one opening is bounded by the framework and, preferably, the at least one opening extends completely through the framework from an inner surface of the framework, when disposed in abutment with the area of the body to be supported, to an outer surface of the framework.

Furthermore, when the support is donned, the framework along its entire boundary with the at least one opening is elastically stretchable between a first initial state and extended states and, when expanded to a said extended state, the framework stores potential energy that is released as kinetic energy upon its return to the initial state. In certain preferred embodiments, interconnected segments of elastomeric material constitute the framework, with the interconnected segments defining these permanent openings in the framework. The interconnected segments may be integrally formed through conventional molding processes or, alternatively, the interconnected segments may be constructed from the joining of segments that are preformed from elastomeric material. Each segment preferably comprises a generally linear segment. A benefit of these openings extending from inner to outer surfaces of the framework is that these openings thereby permit ventilation of portions of the area of the body that are in abutting engagement with the framework. Indeed, the area of the openings to the surface area of the framework preferably has an "open air ratio" of 50% or greater. However, in alternative embodiments that are not shown, the openings in the surface of the framework may not extend entirely through the framework. In such embodiments, the openings comprise cavities formed in the surface of the framework.

Additional aspects include methods of making a support in accordance with any of the foregoing aspects, and methods of using a support in accordance with any of the foregoing aspects.

In addition to the aforementioned aspects and features, the present invention further encompasses the various possible combinations of the foregoing aspects and features.

BRIEF DESCRIPTION OF THE DRAWINGS

A preferred embodiment of the invention will now be described in detail with reference to the accompanying drawings, wherein similar elements are referred to with similar reference numerals.

FIG. 33a is a shaded, plan view of the front of the hinge mechanisms of the support 402 of FIG. 29.

DETAILED DESCRIPTION OF VARIOUS EMBODIMENTS

Figure 1:
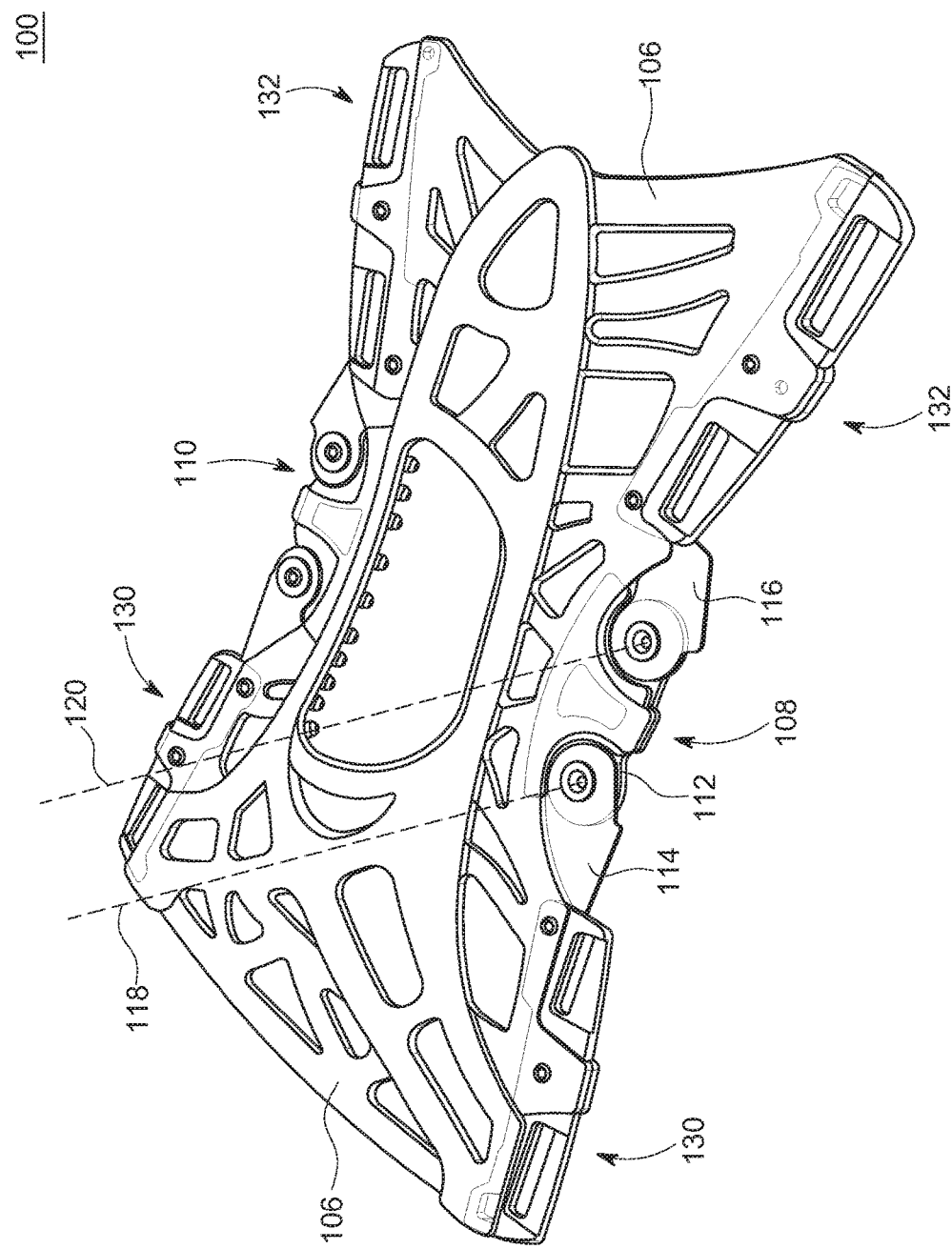
FIG. 1 is a side perspective view of a front of a support 100 in accordance with an embodiment of the invention.

As a preliminary matter, it will readily be understood by one having ordinary skill in the relevant art ("Ordinary Artisan") that the present invention has broad utility and application. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, one or more preferred embodiments of the present invention are next described. The following description of one or more preferred embodiments is merely exemplary in nature and is in no way intended to limit the invention, its implementations, or uses.

A First Embodiment

Turning now to FIGS. 1-17, a support 100 in accordance with a first embodiment of the invention is disclosed.

Figure 2:
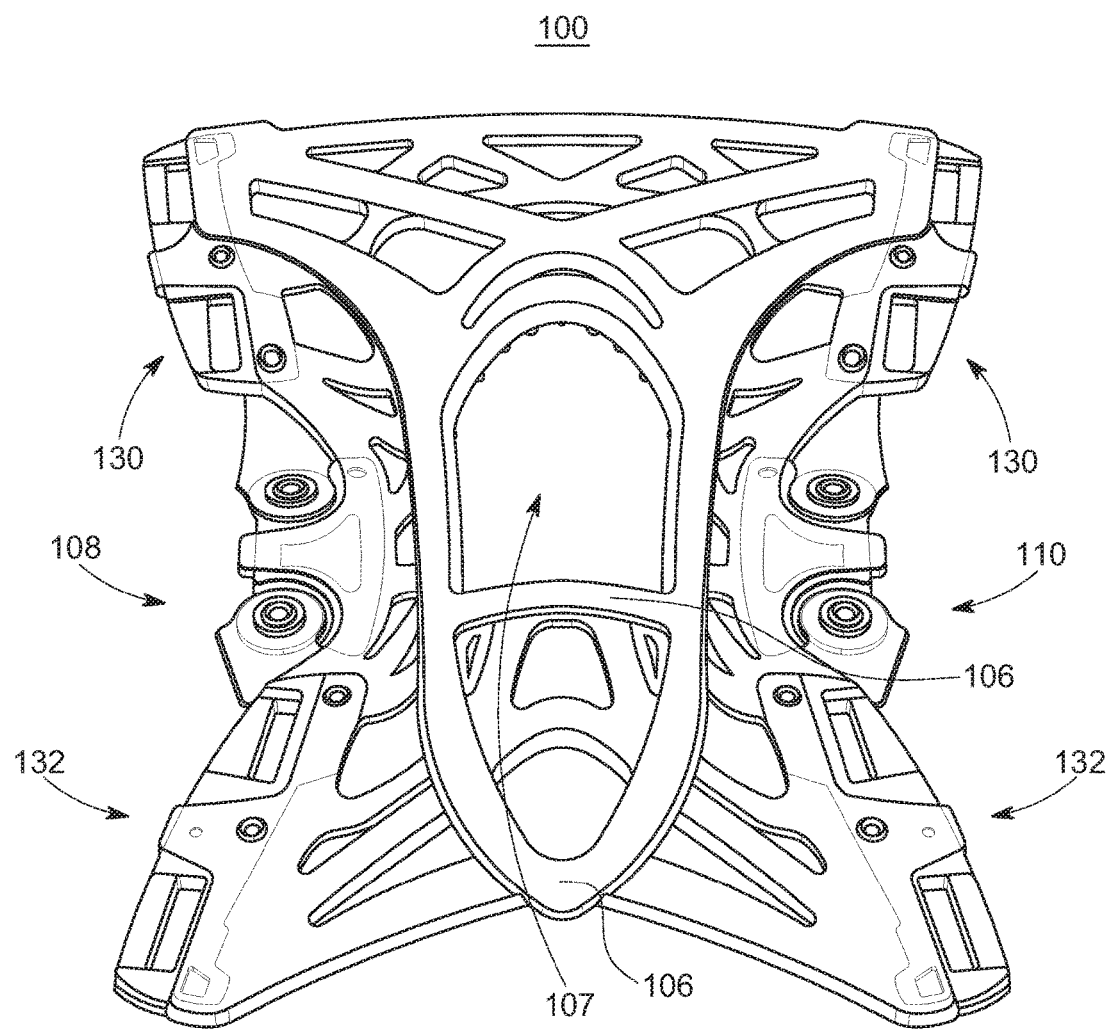
FIG. 2 is a perspective view of the front of the support 100 of FIG. 1.
Figure 3:
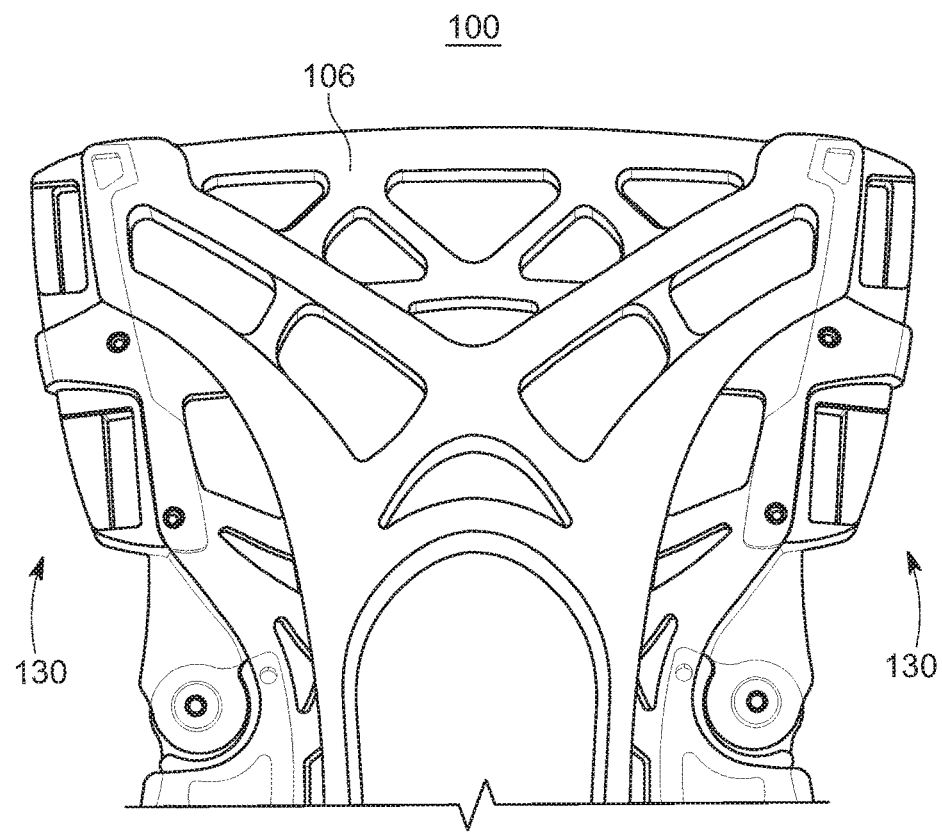
FIG. 3 is a perspective view of an upper half of the front of the support 100 of FIG. 1.
Figure 4:
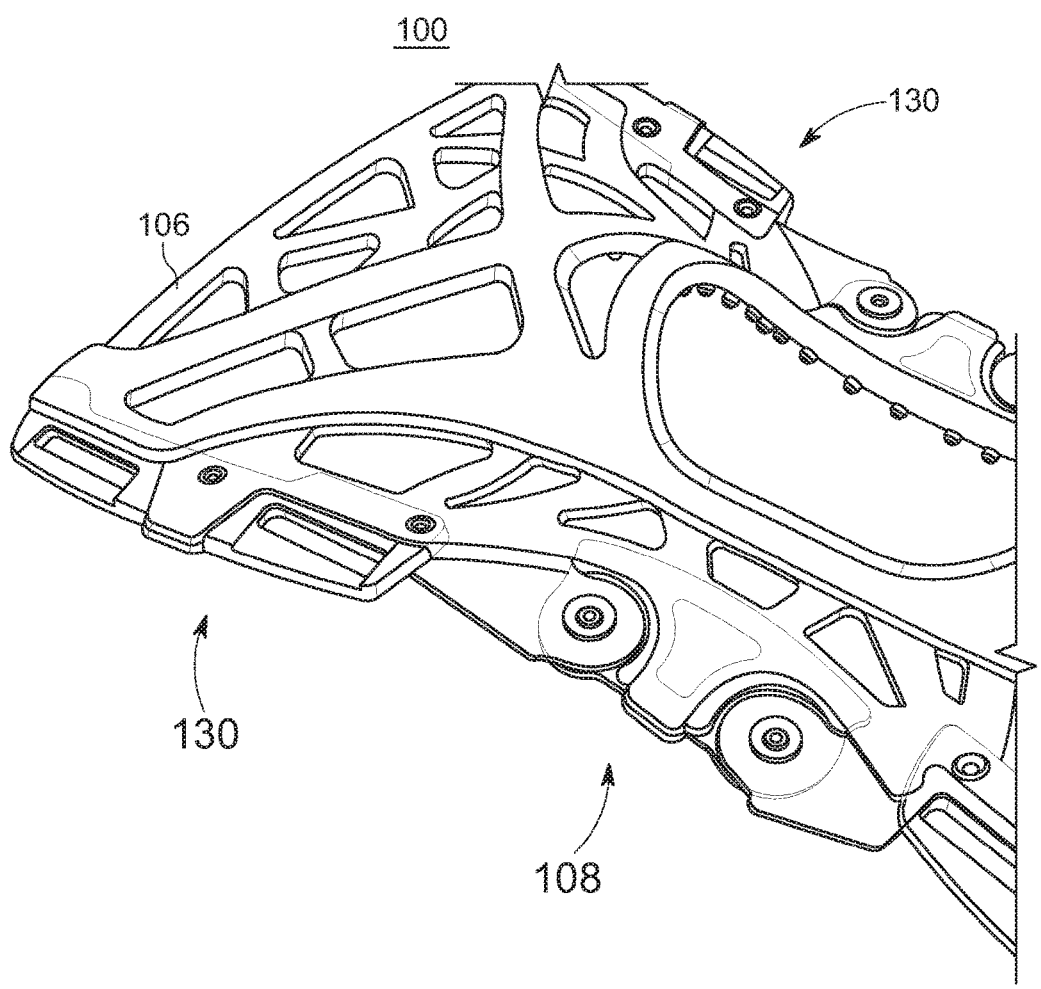
FIG. 4 is a side perspective view of the upper half of the support 100 of FIG. 1.
Figure 5:
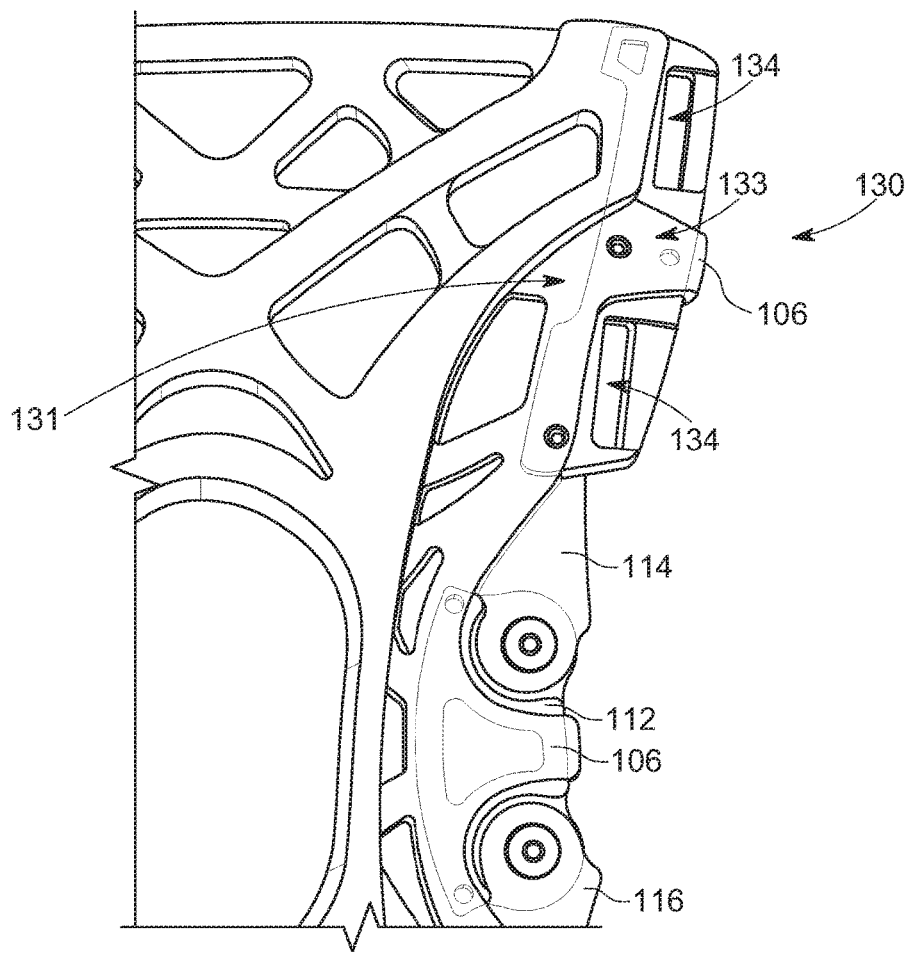
FIG. 5 is a perspective view of an upper right quarter of the front of the support 100 of FIG. 1.
Figure 6:
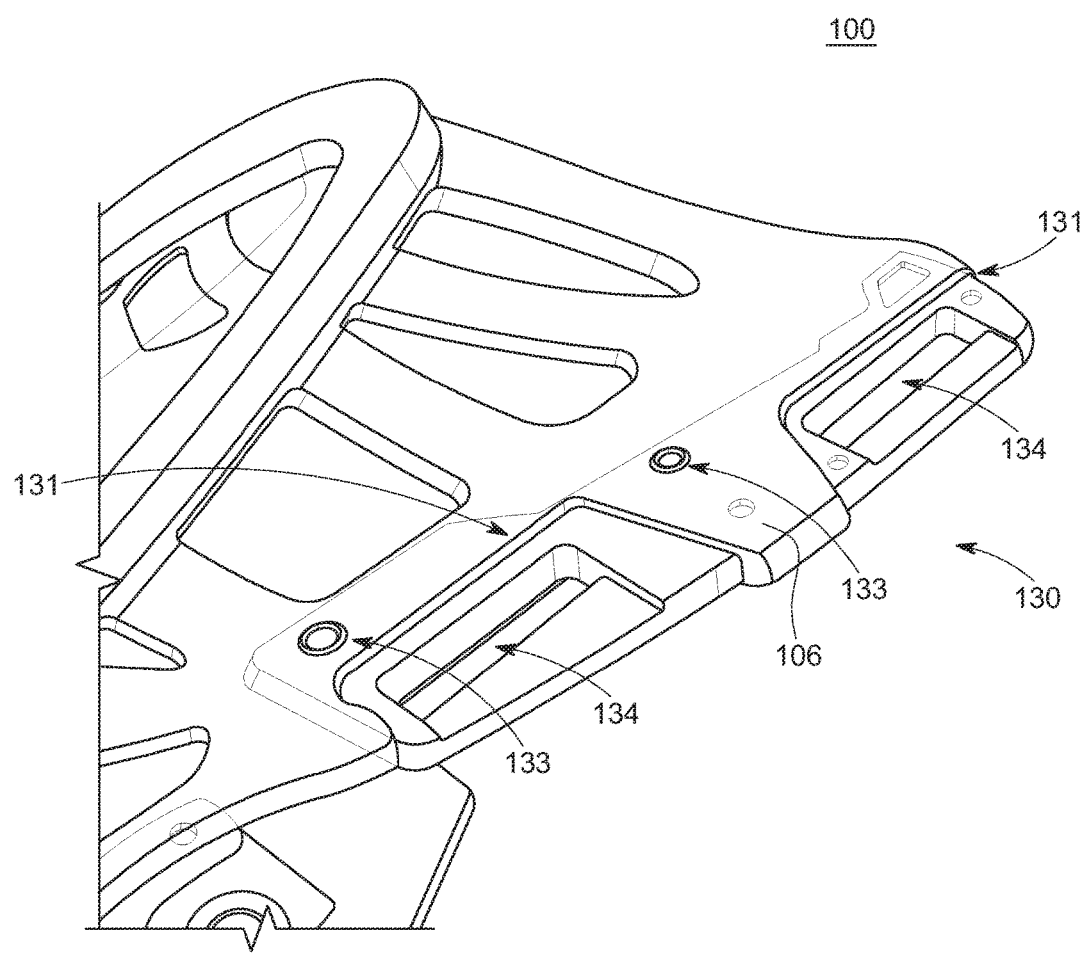
FIG. 6 is a side perspective view of the upper right quarter of the front of the support 100 of FIG that illustrates, in particular, a strap interface component of the support 100.
Figure 7:
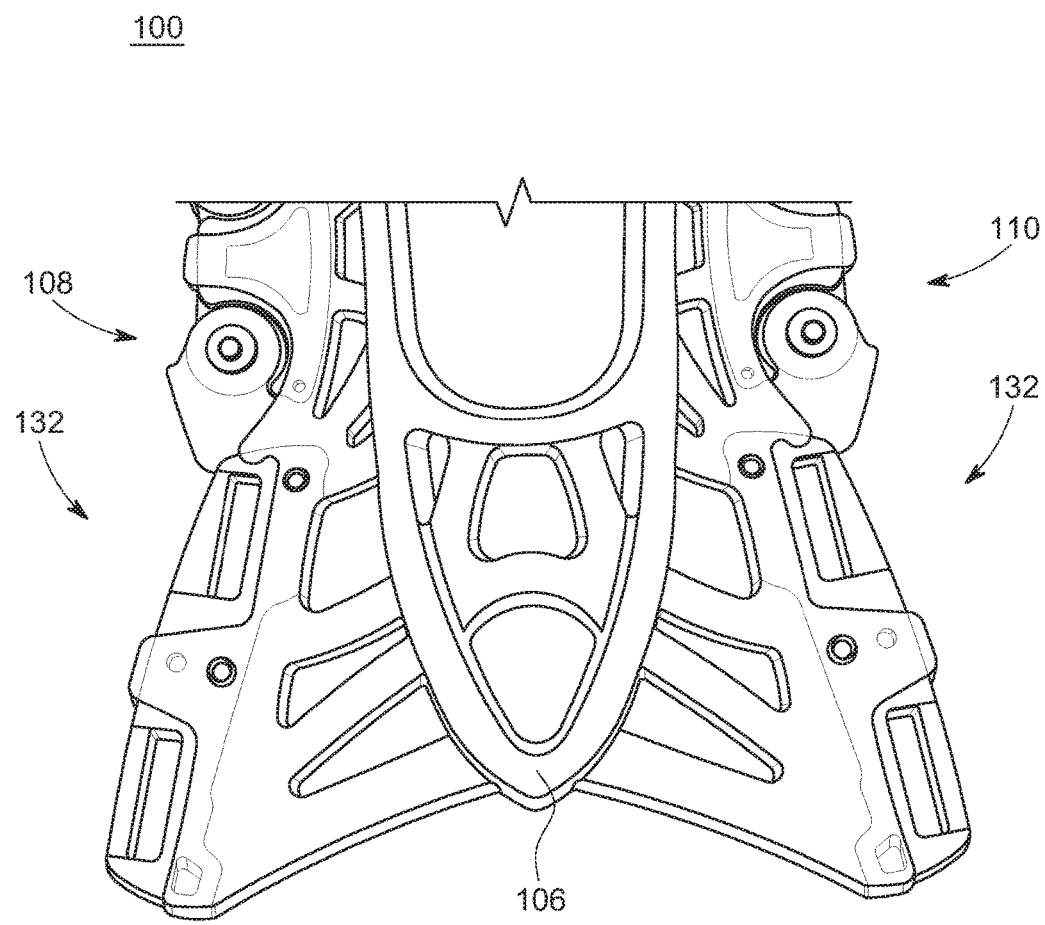
FIG. 7 is a perspective view of a lower half of the front of the support 100 of FIG. 1.
Figure 8:
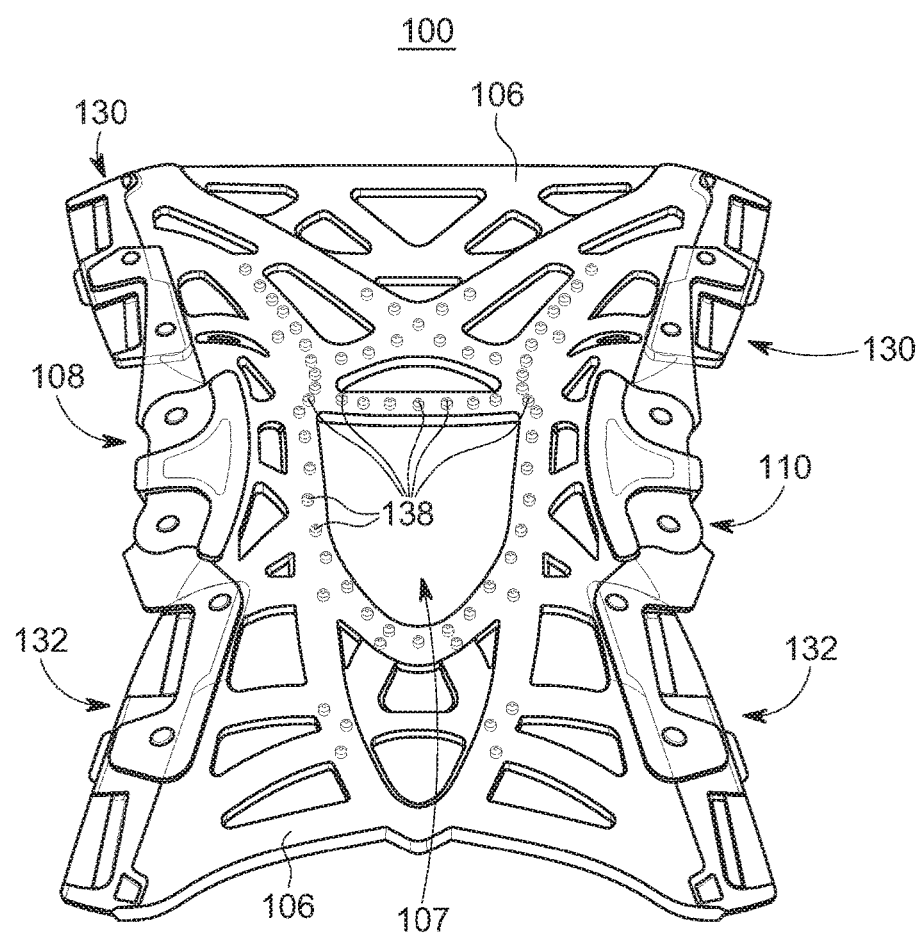
FIG. 8 is a perspective view of a rear of the support 100 of FIG. 1.
Figure 9:
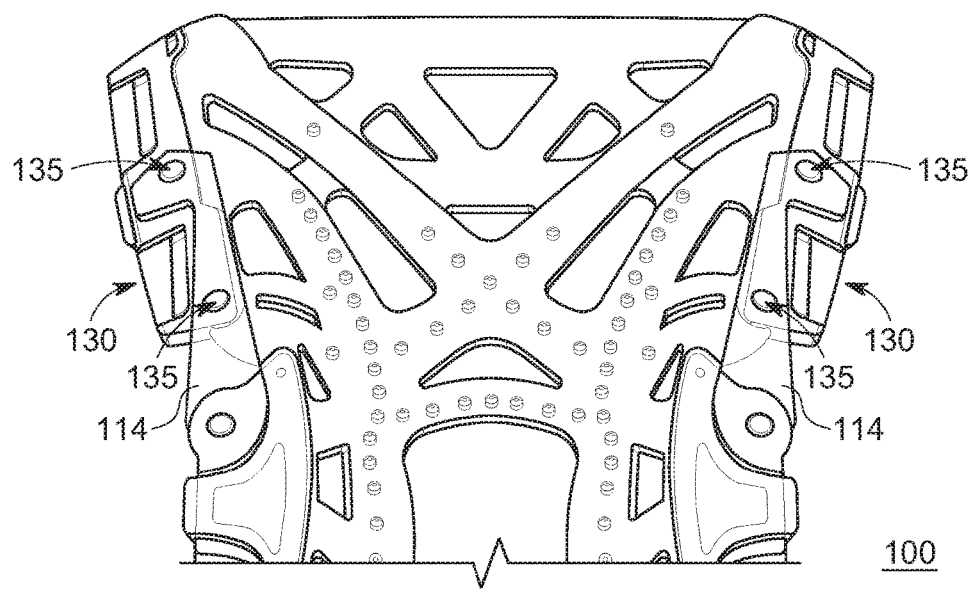
FIG. 9 is a perspective view of an upper half of the rear of the support 100 of FIG. 1.
Figure 10:
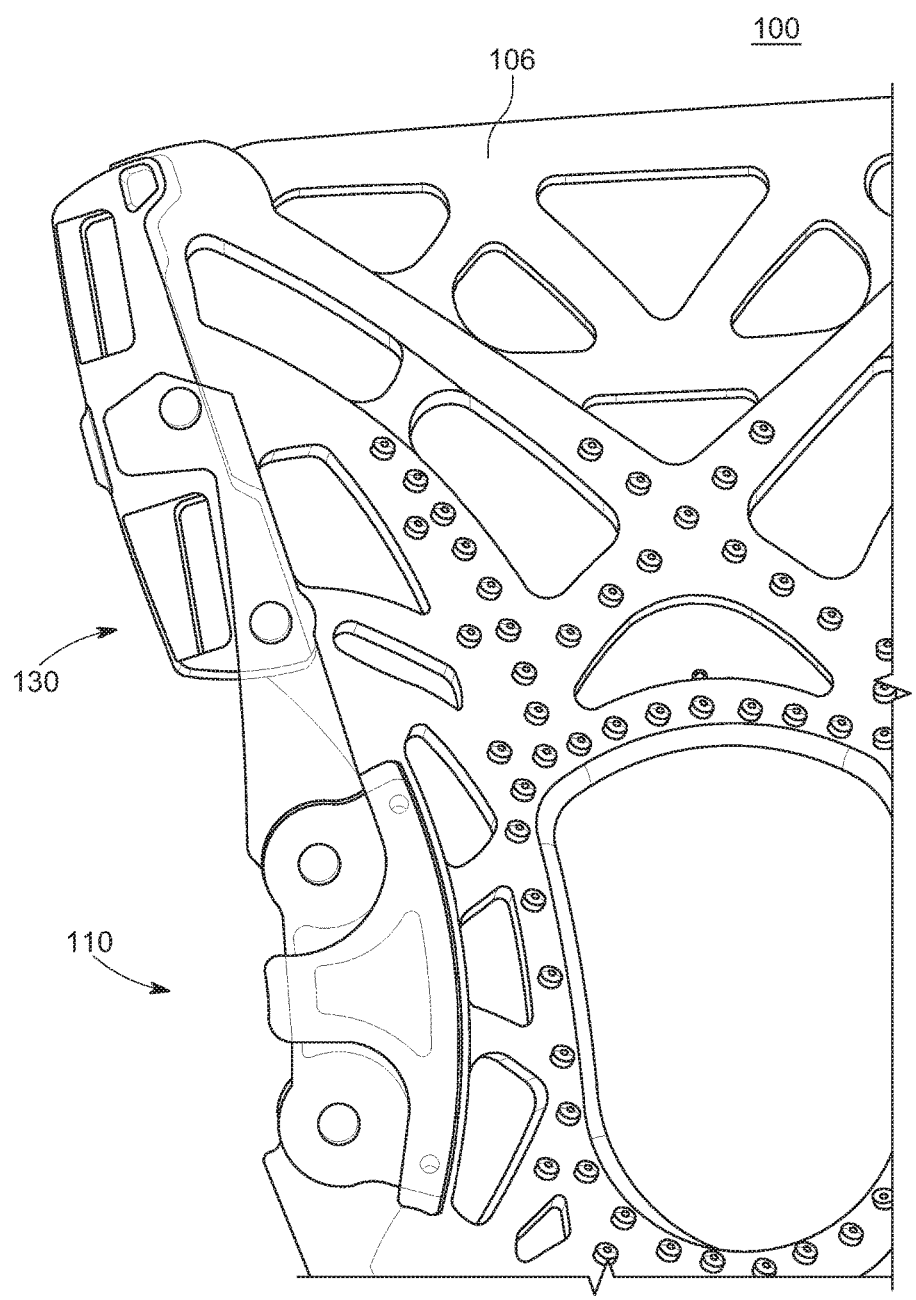
FIG. 10 is a perspective view of an upper left quarter of the rear of the support 100 of FIG. 1.
Figure 11:
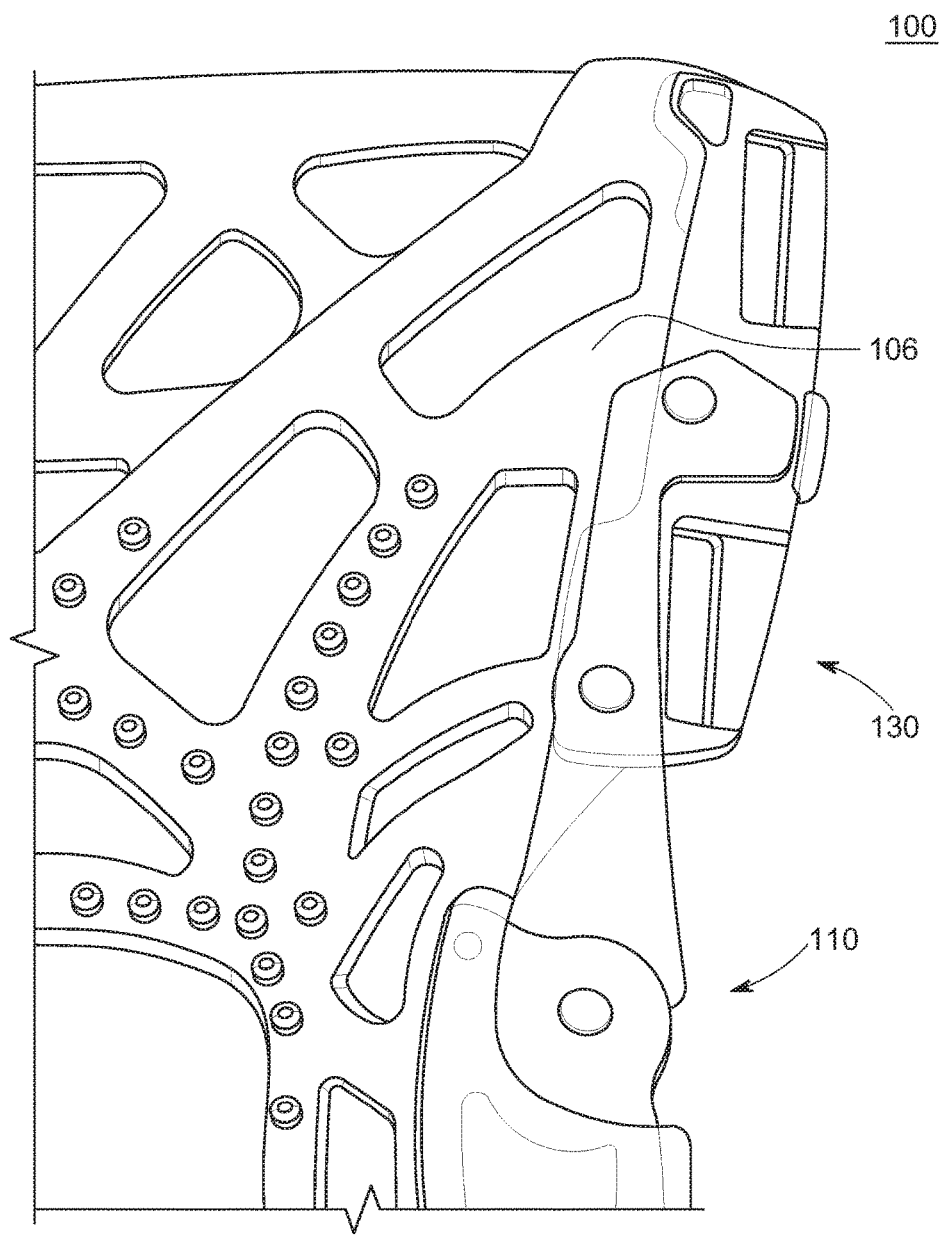
FIG. 11 is a perspective view of an upper right quarter of the rear of the support 100 of FIG. 1.
Figure 12:
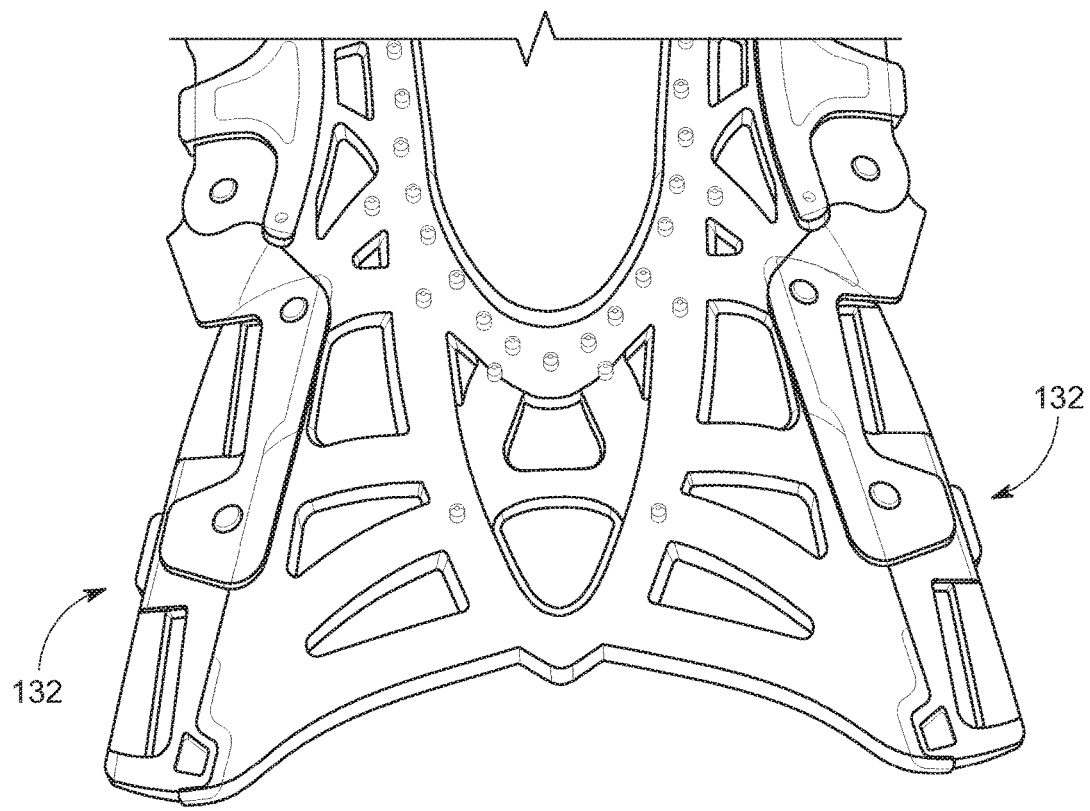
FIG. 12 is a perspective view of a lower half of the rear of the support 100 of FIG. 1.

In this regard, FIG. 1 is a side perspective view of a front of the support 100; FIG. 2 is a perspective view of the front of the support 100; FIG. 3 is a perspective view of an upper half of the front of the support 100; FIG. 4 is a side perspective view of the upper half of the support 100; FIG. 5 is a perspective view of an upper right quarter of the front of the support 100; FIG. 6 is a side perspective view of the upper right quarter of the front of the support 100; FIG. 7 is a perspective view of a lower half of the front of the support 100; FIG. 8 is a perspective view of a rear of the support 100; FIG. 9 is a perspective view of an upper half of the rear of the support 100; FIG. 10 is a perspective view of an upper left quarter of the rear of the support 100; FIG. 11 is a perspective view of an upper right quarter of the rear of the support 100; and FIG. 12 is a perspective view of a lower half of the rear of the support 100.

The support 100 is intended—and is designed and manufactured to be used—for an area of a body having a hinge joint. The support 100 includes a flexible, elastically stretchable framework 106 that is configured to extend across the hinge joint of the area of the body. With reference to support 100, this support is intended and designed for use with the area of a person's knee, and the flexible, elastically stretchable framework 106 is configured to extend across and encompass the knee.

The flexible framework 106 comprises a elastomeric material and, specifically, the framework 106 defines a flexible, elastically stretchable web of elastomeric interconnected members. The elastomeric interconnected members mostly comprise generally linear or curved segments. Furthermore, the framework 106, and the interconnected members in particular, preferably include no internal cavities or pockets of either fluid or gas. The interconnected members define a plurality of permanent openings in the web that extend completely through the framework 106. The openings are "permanent" in that they exist regardless of whether the framework 106 actually is disposed in abutment with the body due to the permanent interconnection of the segments defining the openings. Furthermore, some of these openings are completely bounded by the interconnected members, and the interconnected members defining such an opening constitute a portion of the framework 106 that is stretchable and recoverable about the entire boundary of the opening with the framework 106.

The web includes a larger opening that is symmetrically oriented with respect to the side edges of the framework 106 and that is configured to receive a portion of the knee therethrough and which serves as an alignment opening 107. Specifically, the alignment opening 107 is defined and bounded completely by interconnected members of the framework 106 and is dimensioned and shaped specifically to receive a joint protuberance of the knee. For example, insofar as the framework 106 is adapted to abut a lower thigh and upper calf of a human leg, the alignment opening 107 is shaped to receive the patella of the knee of the leg.

The framework 106 is configured to be stretched and tensioned into abutment with the area of the knee such that the framework 106 conforms to the shape and contour of the area of the knee when stretched and tensioned. In particular, the framework 106 has a relaxed state when not stretched and tensioned as shown, for example, in FIG. 1, wherein the support 100 rests upon a wood table. In this state, the framework 106 does not conform to the shape and contour of the area of the knee.

It will be appreciated by the Ordinary Artisan that, due to the elastically stretchable nature of the framework, the support allows flexing of a hinge joint of the body and, in fact, contributes to such flexing. In this regard, because at least portions of the framework 106 are elastically stretchable, flexing of the knee from an extended position to a retracted or bent position results in the expansion of the framework 106 and storage of potential energy therein that is released as kinetic energy when the knee is returned to the extended position. The support 100 thus is not an immobilizing support but, instead, the support 100 is a potentiating support for the area of the body including the knee joint insofar as the framework 106 is capable of dynamically biasing a joint toward a particular state of extension or flexion.

In particular, because of the elastically stretchable and recoverable nature of the material of the framework 106, the framework 106 stores potential energy when stretched and tensioned that is released as kinetic energy upon transitioning of the framework 106 back toward a relaxed (or less tensioned) state. This correlates to transitioning of hinge mechanisms 108,110 (discussed next) from a first position corresponding to a flexed or bent position of the knee, to a second position of the hinge mechanisms 108,110 corresponding to a less flexed or bent (i.e., more extended) position of the knee.

The support 100 further includes a pair of hinge mechanism 108,110. Each hinge mechanisms 108,110 is affixed to the framework 106 and is structurally the same. Thus, while the detailed structure of hinge mechanism 108 will now be described, it will equally apply to hinge mechanism 110.

Figure 13:
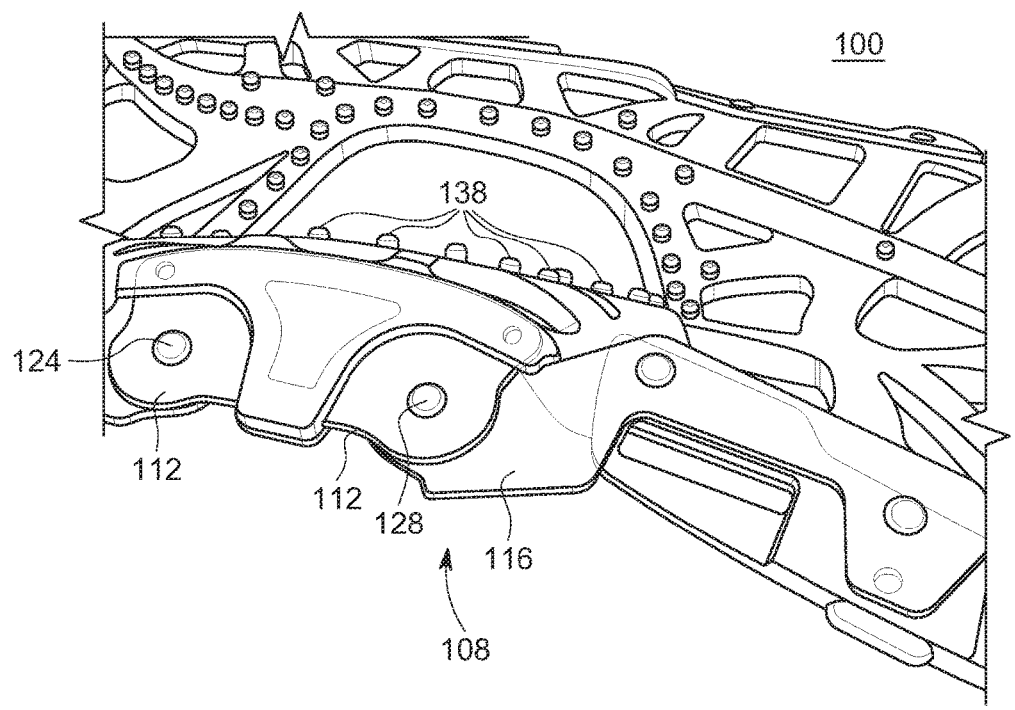
FIG. 13 is a side perspective view of a rear, lower portion of a hinge mechanism of the support 100 of FIG. 1.
Figure 14:
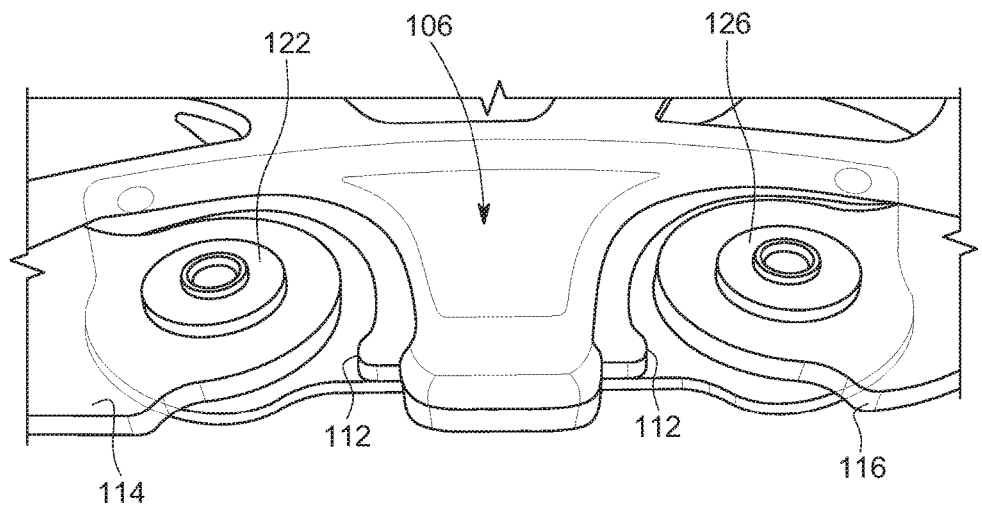
FIG. 14 is a side perspective view of a front, middle portion of a hinge mechanism of the support 100 of FIG. 1.
Figure 15:
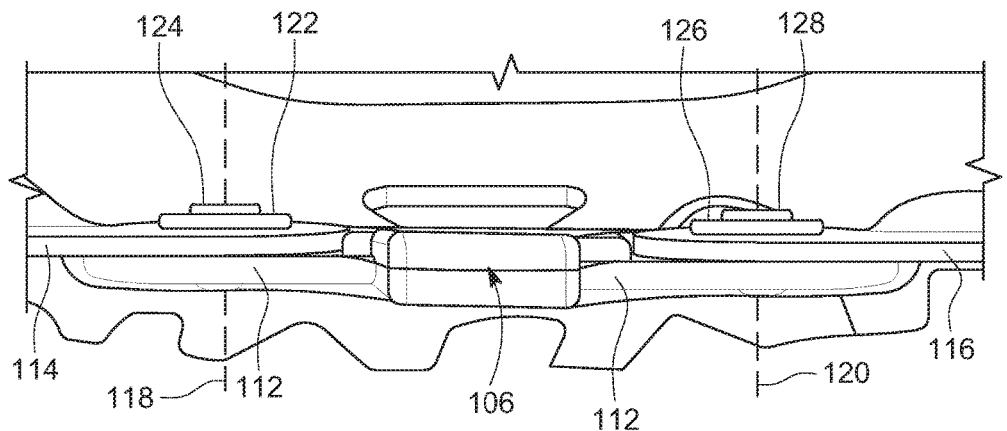
FIG. 15 is a side perspective view of the front, middle portion of the hinge mechanism of FIG. 14.
Figure 16:
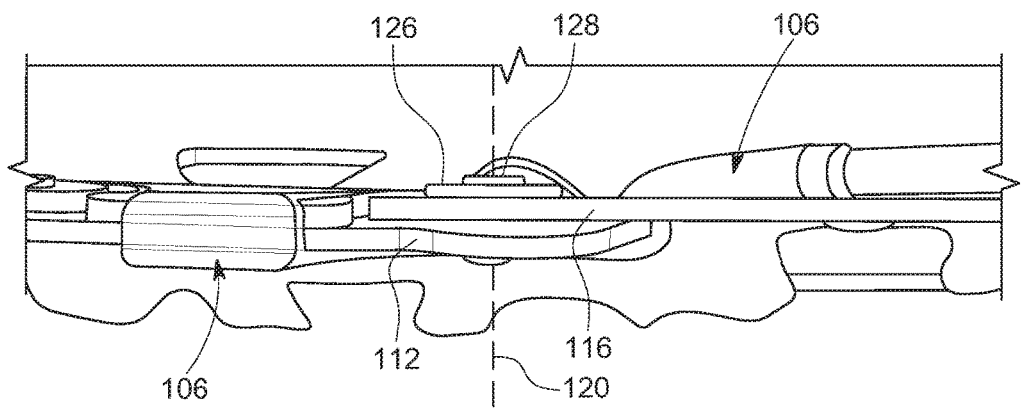
FIG. 16 is a side perspective view of part of the front, middle portion of the hinge mechanism of FIG. 14.
Figure 17:
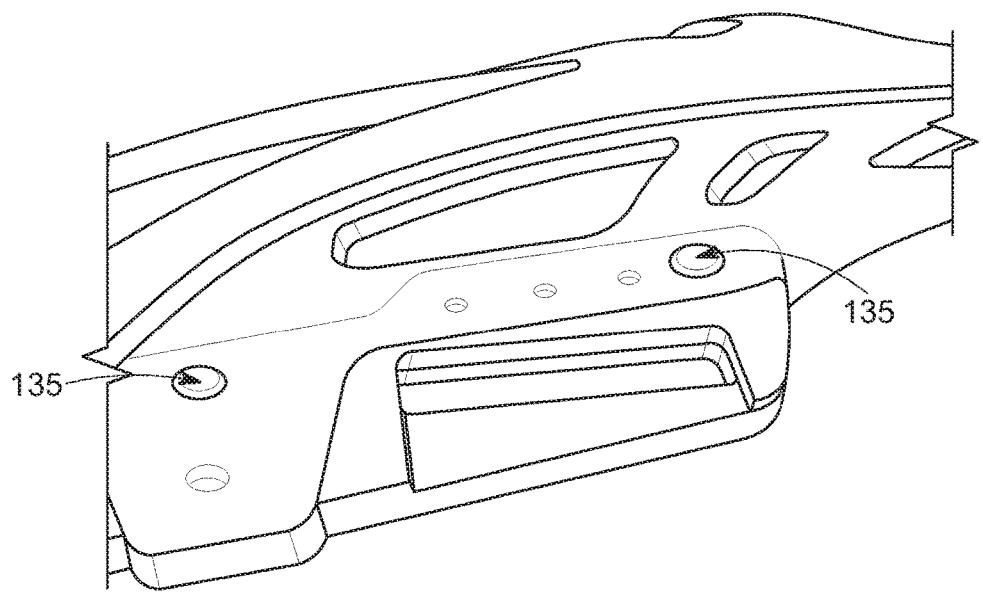
FIG. 17 is a side perspective view of part of a strap interface component of the support 100 of FIG. 1 that illustrates, in particular, the strap interface component at least partially embedded in a material of the framework of the support 100.

Hinge mechanism 108 includes a strut component 112 and first and second arm components 114,116. Each of these components preferably is generally planar, as will be appreciated from inspection of FIGS. 13-16, wherein FIG. 13 is a side perspective view of a rear, lower portion of the hinge mechanism 108; FIG. 14 is a side perspective view of a front, middle portion of the hinge mechanism 108; FIG. 15 is a side perspective view of the front, middle portion of the hinge mechanism 108; and FIG. 16 is a side perspective view of part of the front, middle portion of the hinge mechanism 108.

As perhaps best shown in FIGS. 13-16, the first arm component 114 is connected to the strut component 112 such that the first arm component 114 is rotatable relative to the strut component 112 about a first pivot axis 118. As opposed to, for example, a continuous hinge, the strut component 112 and the first arm component 114 are mechanically connected, and the first pivot axis 118 is fixed relative to each of these components. Consequently, the first arm component 114 is rotatable relative to the strut component 112 only about a first pivot axis 118.

Similar to the first arm component 114, the second arm component 116 is connected to the strut component 112 such that the second arm component 116 is rotatable relative to the strut component 112 about a second pivot axis 120. Moreover, the strut component 112 and the second arm component 116 are mechanically connected, and the second pivot axis 118 is fixed relative to each of these components. Consequently, the second arm component 116 is rotatable relative to the strut component 112 only about the second pivot axis 120.

The hinge mechanism 108 is located along a first side edge of the framework 106, and the hinge mechanism 110 is located along a second, opposite side edge of the framework 106. The hinge member 108, and the strut component 112 in particular, is partially embedded in a material of the framework 106. Indeed, as perhaps best seen in FIGS. 14 and 15, a material of the framework 106 actually encompasses and completely encircles a middle portion of the strut component 112. The strut component 112 may be so embedded within the material of the framework during the manufacture of the support by molding or otherwise forming the framework 106 directly onto the strut component 112. Similarly, each of the first and second arm components 114,116 may be at least partially embedded in a material of the framework 106; however, none of the first and second arm components 114,116 are even partially embedded in a material of the framework 106 in the support 100 as shown.

Each hinge mechanism 108,110 is arranged relative to the framework 106 such that the strut component of the each hinge mechanism extends with the framework across the hinge joint such that the first pivot axis of each hinge mechanism 108,110 is located on one side of the hinge joint and the second pivot axis of each hinge mechanism 108,110 is located on the other, opposite side of the hinge joint when the support is worn. In particular, the strut components of each hinge mechanism 108,110 are configured to extend with the framework 106 across the knee joint such that the first pivot axis of each hinge mechanism 108,110 is located above the knee and the second pivot axis of each hinge mechanism 108,110 is located below the knee.

With further regard to hinging mechanism 108, a first hinging member 122 connects the first arm component 114 to the strut component 112, the first hinging member 122 including a cylindrical portion 124 in abutment with which the first arm component 114 and strut component 112 rotate. Likewise, a second hinging member 126 connects the second arm component 116 to the strut component 112, the second hinging member 126 including a cylindrical portion 128 in abutment with which the second arm component 116 and strut component 112 rotate. As will be appreciated, the first pivot axis 118 axially extends through the cylindrical portion 124 of the first hinging member 122, and the second pivot axis 120 axially extends through the cylindrical portion 128 of the second hinging member 126.

As will be appreciated from the drawings and above disclosure, each of the components of the hinge mechanism are distinct from one another. Moreover, the components 112,114,116 of each hinge mechanism 108,110 are preferably rigid, in that each provides a degree of rigidity in a local area of the framework 106, especially proximate a local peripheral area along longitudinal sides of the framework 106 within which such respective component may be attached and/or embedded or otherwise may be affixed.

The support 100 further includes, along each side of the framework 106, first and second strap interface components 130,132. The strap interface components 130,132 are structurally the same. Thus, while the detailed structure of a first strap interface component 130 will now be described, such discussion equally will apply to the second strap interface component 132.

The strap interface component 130 is affixed to the framework 106. In this respect, the first strap interface component 130 is at least partially embedded in a material of the framework 106 (as perhaps best seen at 131 in FIG. 5), and/or the first strap interface component 130 is riveted or otherwise fastened to the material of the framework 106 (as perhaps best seen at 133 in FIG. 5).

While affixed to the framework 106, the first strap interface component 130 is connected to the first arm component 114 and the second strap interface component 132 is connected to the second arm component 116 of one of the hinge mechanisms 108,110. In this respect, each strap interface component 130,132 is riveted or otherwise fastened at 135 to the respective arm component 114,116 in fixed disposition relative thereto, as perhaps best seen in FIGS. 9 and 12 as well as FIG. 17, wherein a side perspective view of part of a strap interface component is shown. As will be appreciated from examination of these drawings, each strap interface component is not only riveted or otherwise fastened to an arm component but also is fastened to the framework at 135 by the rivet or other fastener.

The first strap interface components 130 also each defines at least one opening therein that is configured to receive therethrough a strap for attachment of the framework 106 to the area of the knee. In particular, the first strap interface components 130 each defines two openings 134 through which straps are received for attachment of the upper portion of the framework 106 to the area of the leg above the knee. Likewise, the second strap interface components 132 each defines two openings through which straps are received for attachment of the lower portion of the framework 106 to the area of the leg below the knee.

The front side of the framework 106 as shown in FIGS. 1-7 generally is the same as the back side of the framework 106 as shown in FIGS. 8-13; however, unlike the surface of the front side of the framework 106, selected areas of the surface of the back side of the framework 106 include raised protuberances (representatives ones of which are indicated by 138 in the drawings), which protuberances are intended to increase the frictional abutment of the framework 106 with the area of the knee when the support 106 is donned. The protuberances 138 serve to position and hold the support in abutment with the area of the body including the spanning of the hinge joint.

In use of the support 100 in accordance with the invention, the support 100 is positioned against the body such that the support 100 extends across the knee and such that the second strut components 112 of the first and second hinge mechanisms 108,110 extend with the framework 106 across the knee joint, with the first pivot axes 118 of the first and second hinge mechanisms 108,110 being located above the knee joint and with the second pivot axes 120 of the first and second hinge mechanisms 108,110 being located below the knee joint. The support 100 is further positioned such that the strut components 112 of the first and second hinge mechanisms extend on opposite sides of the hinge joint of the body. The positioning of the support 100 includes tensioning the framework 106 in abutment with the area of the knee and fastening the support 100 to the body on opposite sides of the knee such that the framework 106 is held in tension in its abutment with the area of the body including the knee. In so doing, the elastically stretchable framework 106 preferably conforms to the surface contour of the area of the knee as a result of the tensioning.

The support 100 is fastened to the body in a conforming position via a fastening mechanism (not shown in FIGS. 1-17) that is detachably connected to and applies tension at different points of attachment to the framework 106 such that the framework 106 is expanded and tensioned in its abutment with the area of the body and, in particular, in the area of the knee. Furthermore, the fastening mechanism preferably includes fastening straps with Velcro fasteners. The straps are received and extend through the strap openings 134 of the strap interface components of the support 100.

The combination of the support 100 and fastening mechanism is referred to herein as a support assembly. The support assembly optionally may include a sleeve having a open-ended tubular structure. Such a sleeve preferably would extend around and completely encircle a leg and would be constructed of a soft material. The sleeve itself also may be elastically stretchable. Exemplary materials include synthetic and natural fabrics, monolayer and multi-layered textiles, woven and non-woven planar materials, neoprene bonded to fabric, spandex and elastane, felt, and natural and synthetic chamois. At least a portion of the sleeve would be disposed between the framework and a portion of the leg proximate the knee and would thereby serve as a liner for the framework.

A support assembly is included in the drawings in connection with a second preferred embodiment, discussed next, and the discussion and use of the fastening mechanism and sleeve thereof are equally applicable with respect to use with the support 100.

A Second Embodiment

Turning now to FIGS. 18-22, a support assembly 200 in accordance with a second embodiment of the invention is disclosed.

Figure 18:
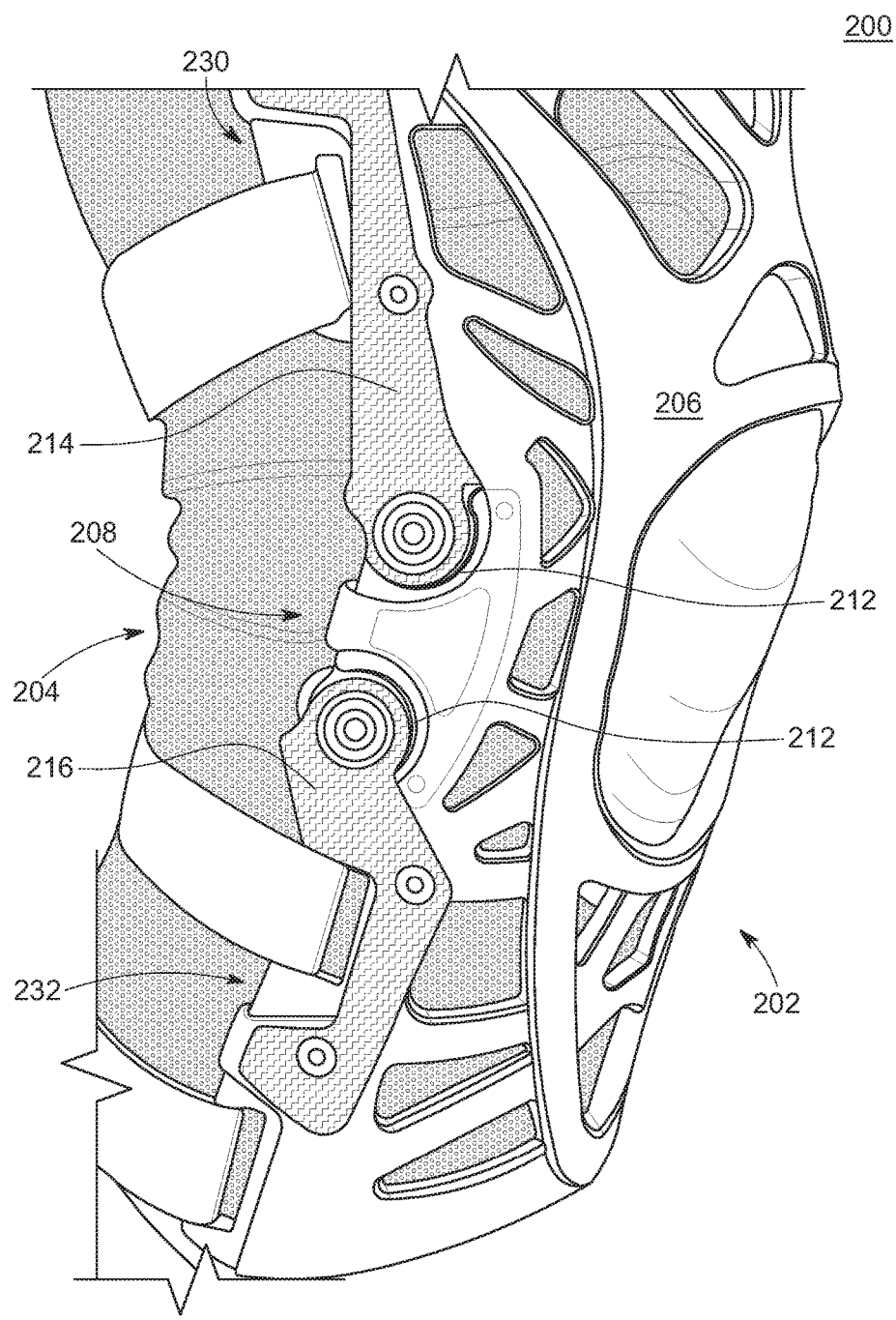
FIG. 18 is a side perspective view of a support assembly 200 being worn in accordance with an embodiment of the invention.
Figure 19:
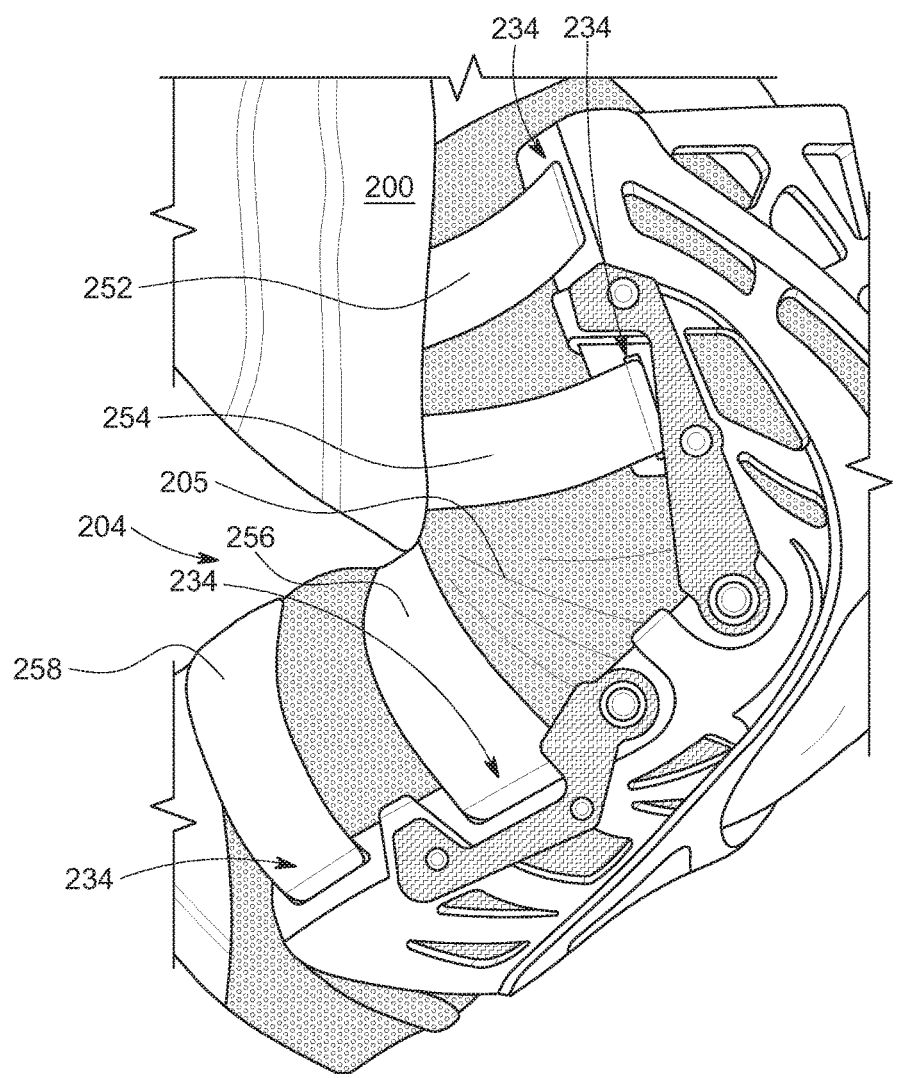
FIG. 19 is another side perspective view of the support assembly 200 of FIG. 18 being worn in accordance with an embodiment of the invention.
Figure 20:
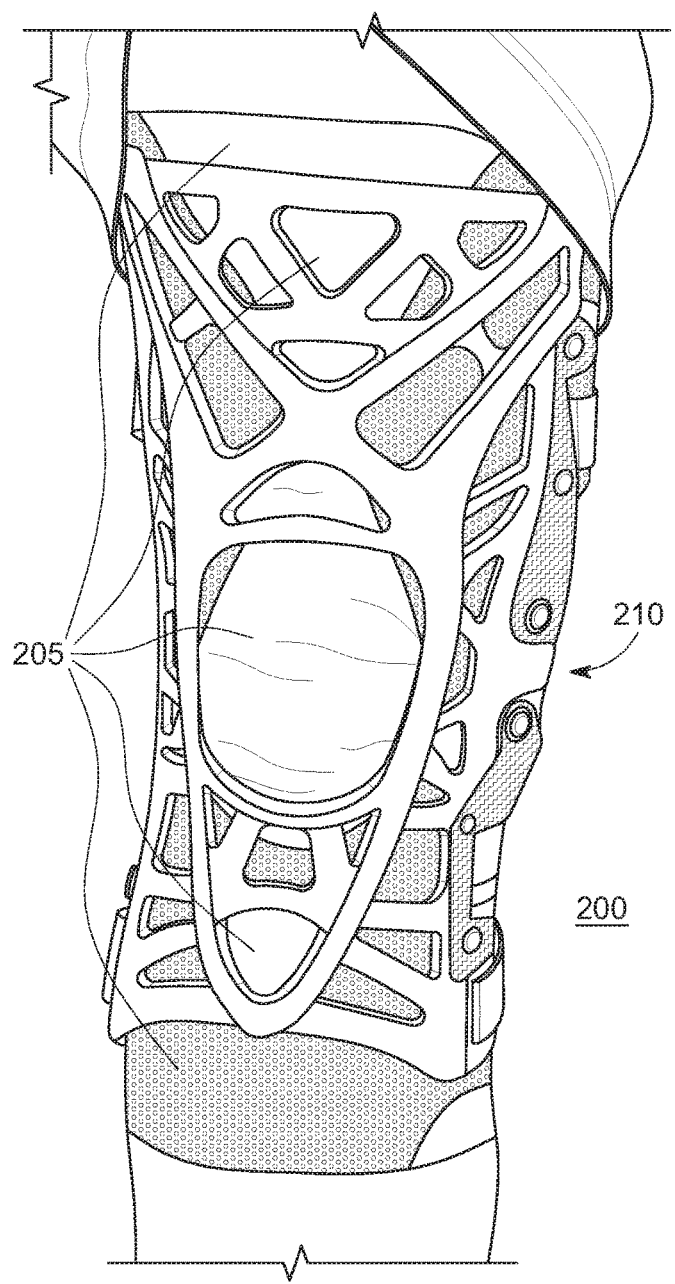
FIG. 20 is a perspective view of a front of the support assembly 200 of FIG. 18 being worn in accordance with an embodiment of the invention.
Figure 21:
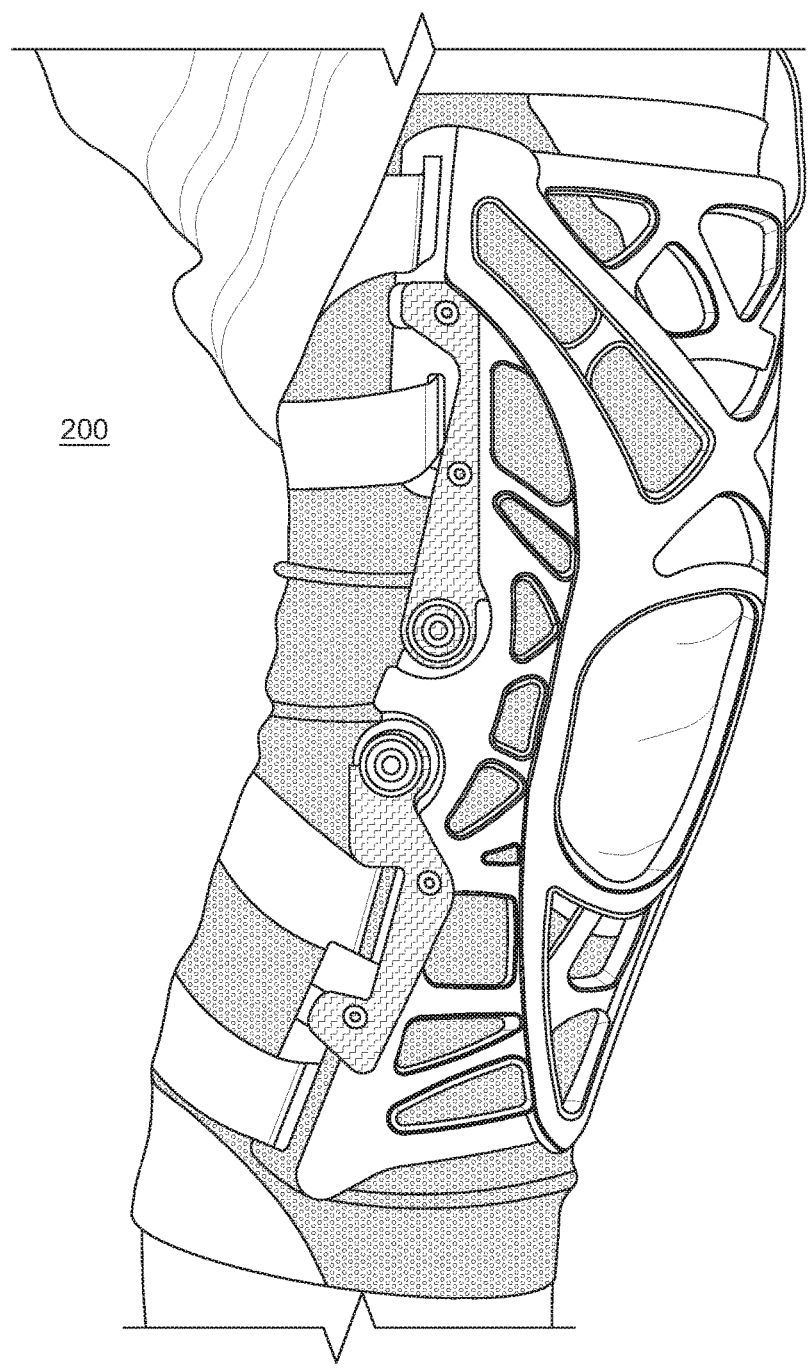
FIG. 21 is another side perspective view of the support assembly 200 of FIG. 18 being worn in accordance with an embodiment of the invention.
Figure 22:
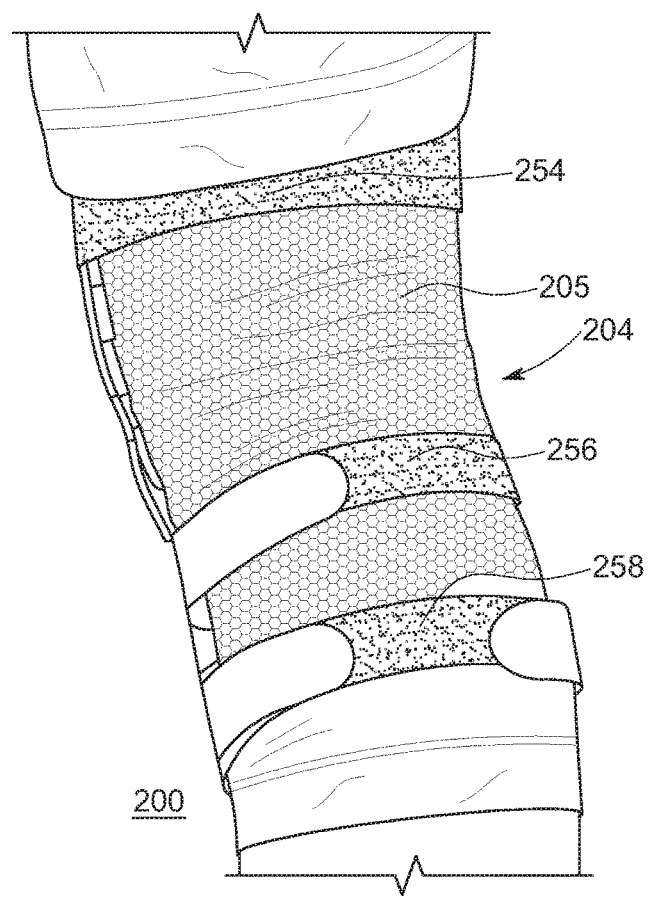
FIG. 22 is a perspective view of the rear of the support assembly 200 of FIG. 18 being worn in accordance with an embodiment of the invention.

In this regard, FIG. 18 is a side perspective view of the support assembly 200 being worn in accordance with an embodiment of the invention; FIG. 19 is another side perspective view of the support assembly 200 being worn; FIG. 20 is a perspective view of a front of the support assembly 200 being worn; FIG. 21 is another side perspective view of the support assembly 200 being worn; and FIG. 22 is a perspective view of the rear of the support assembly 200 being worn.

With regard to the support assembly 200 of the second embodiment, the support assembly 200 includes support 202 and fastening mechanism 204 as well as a sleeve 205 (best seen in FIG. 22) that serves as a liner for the framework 206 of the support 202.

The support 202 and the framework 206 are generally the same structurally as the support 100 and framework 106 discussed supra with regard to the first preferred embodiment and FIGS. 1-17, and in the interests of brevity, the similarities are not repeated. The support 202 and framework 206 differ from the support 100 and framework 106 of FIGS. 1-17 in that the first arm component 214 of each of the hinge mechanisms 208,210 overlays a respective first strap interface component 230 of the upper portion of the support 202; and in that the second arm component 216 of each of the hinge mechanisms 208,210 overlays a respective second strap interface component 232 of the upper portion of the support 202.

In this respect, the strut component 212 of each hinge mechanism 208,210 generally is coplanar with the first and second strap interface components 230,232, whereas the strut component 112 of each hinge mechanism 108,110 generally is not coplanar with the first and second strap interface components 130,132 in the support 100, as shown for example in FIGS. 6, 10, and 12. In the support 100, the strut component 112 of each hinge mechanism 108,110 and the first and second strap interface components 130,132 are located on opposite sides of the arm components 114,116.

The fastening mechanism 204 is perhaps best shown in FIGS. 19 and 22 and includes four straps 252,254,256,258. Each of the straps includes opposite ends having Velcro fasteners arranged such that each end may be passed through a respective opening 234 formed in the strap interface components 230,232 and folded back and attached to itself.

The fastening mechanism 204 applies tension at different points of attachment to the framework 106, via the fastener interface components 230,232, such that the framework 106 is expanded and tensioned in its abutment with the area of the body and, in particular, in the area of the knee. In particular, the fastening straps 252,254,256,258 are grasped and manually pulled at desired levels of tension, whereby the support is highly adjustable. The resulting tensional forces from the straps 252,254,256,258 are applied at multiple points of attachment along the opposite sides of the framework 206, whereby the framework 206 is elastically stretched and the surface thereof is shaped to fit the abutted area of the body including the knee.

As will be appreciated from the drawings, the framework 206 of the support 202 does not overlap itself when worn as shown.

A Third Embodiment

Turning now to FIGS. 23-27, a support assembly 300 in accordance with a third embodiment of the invention is disclosed.

Figure 23:
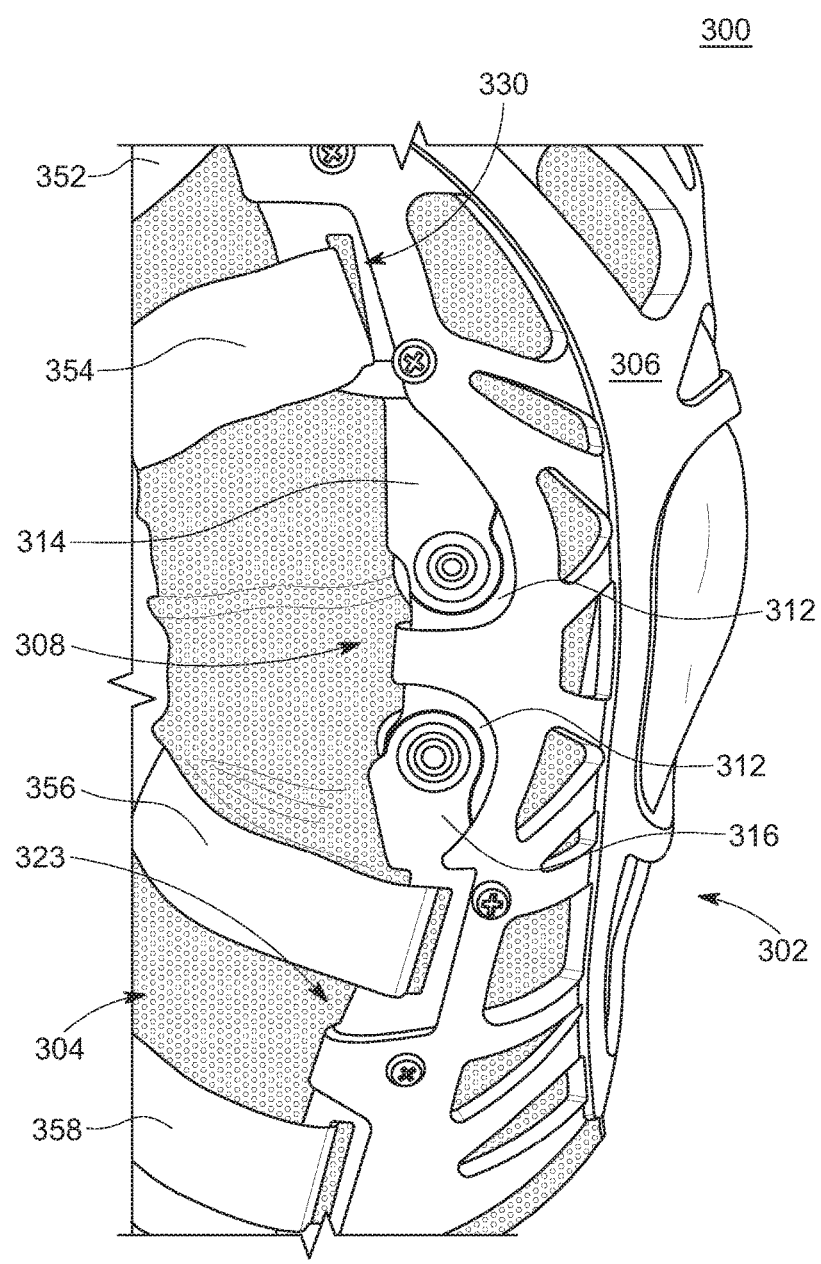
FIG. 23 is a side perspective view of a support assembly 300 being worn in accordance with an embodiment of the invention.
Figure 24:
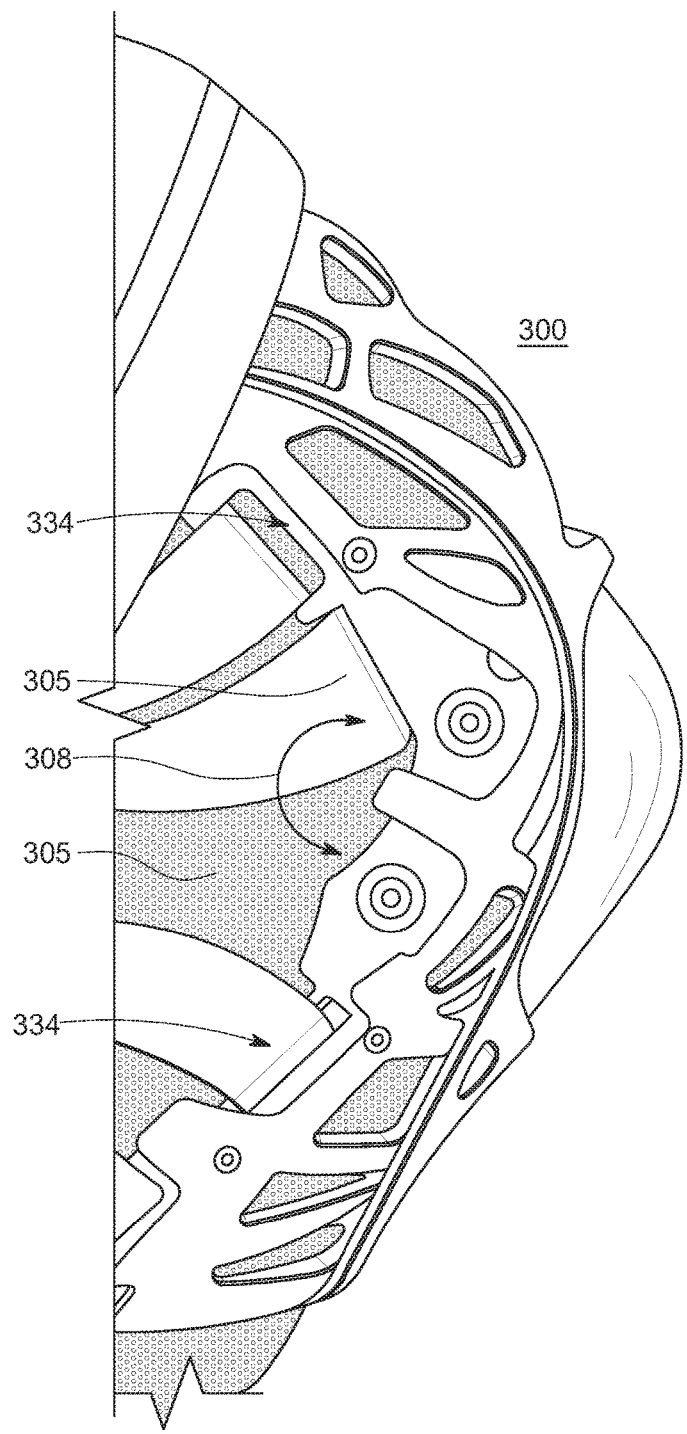
FIG. 24 is another side perspective view of the support assembly 300 of FIG. 23 being worn in accordance with an embodiment of the invention.
Figure 25:
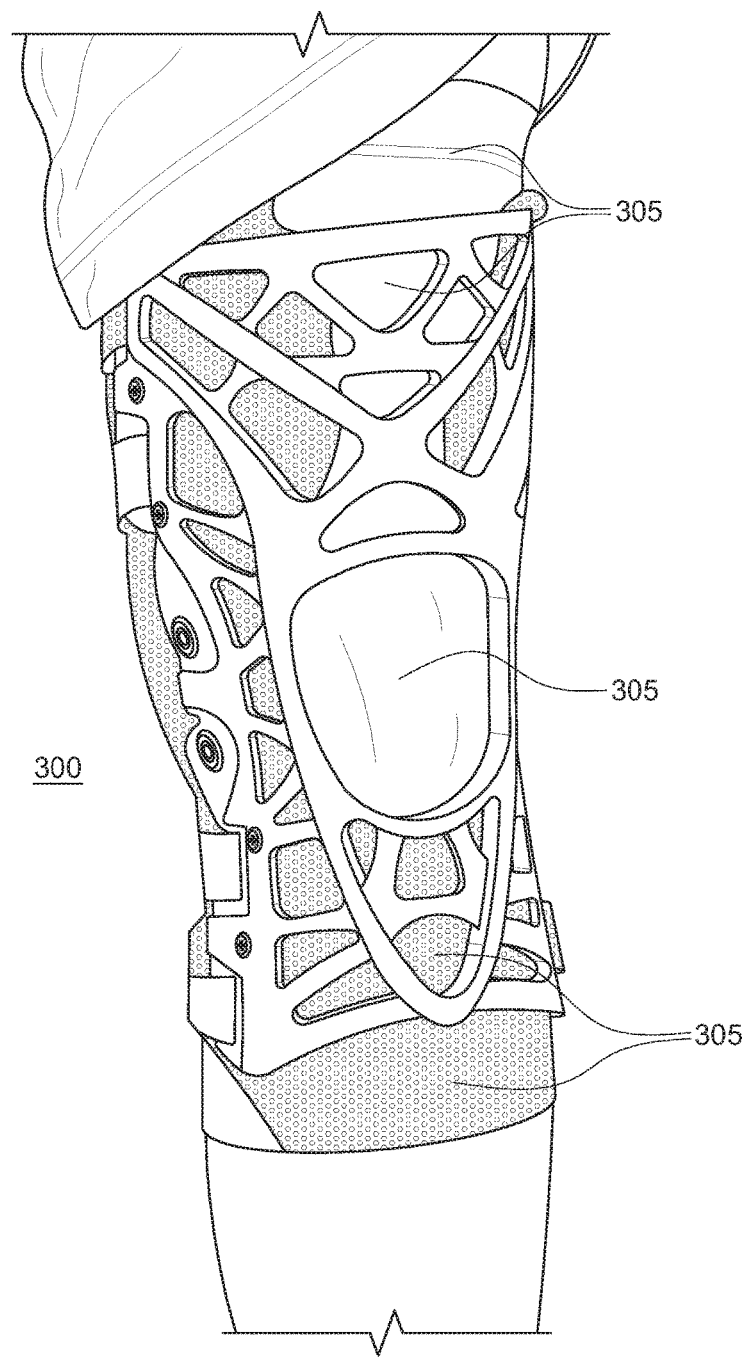
FIG. 25 is a perspective view of a front of the support assembly 300 of FIG. 23 being worn in accordance with an embodiment of the invention.
Figure 26:
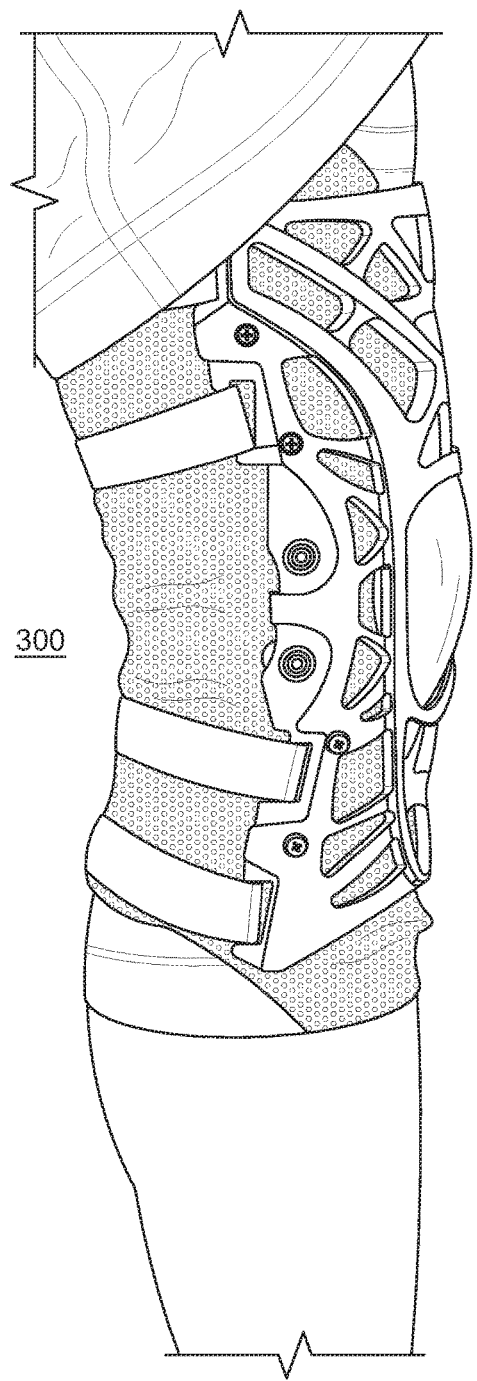
FIG. 26 is another side perspective view of the support assembly 300 of FIG. 23 being worn in accordance with an embodiment of the invention.
Figure 27:
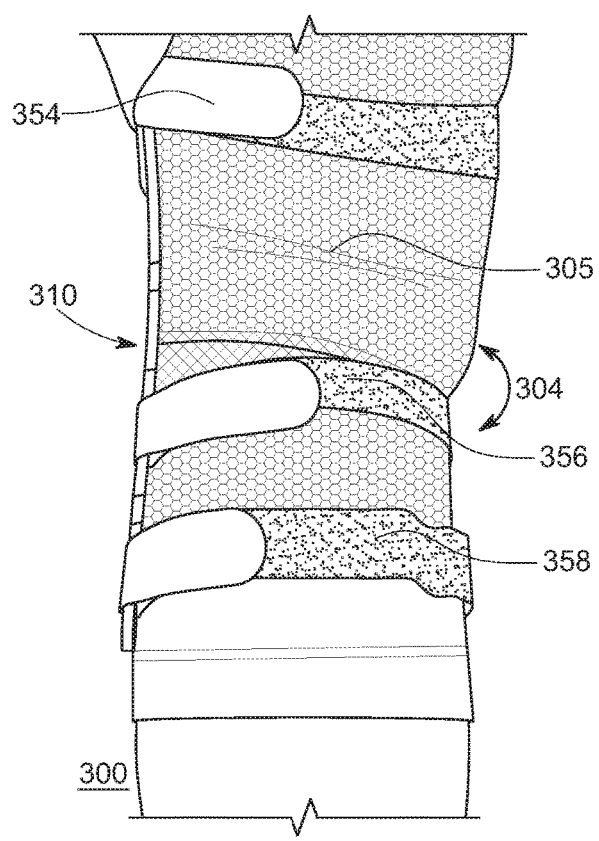
FIG. 27 is a perspective view of the rear of the support assembly 300 of FIG. 23 being worn in accordance with an embodiment of the invention.

In this regard, FIG. 23 is a side perspective view of a support assembly 300 being worn; FIG. 24 is another side perspective view of the support assembly 300 being worn; FIG. 25 is a perspective view of a front of the support assembly 300 of FIG. 23 being worn; FIG. 26 is another side perspective view of the support assembly 300 being worn; and FIG. 27 is a perspective view of the rear of the support assembly 300 of FIG. 23 being worn.

With regard to the support assembly 300 of the third embodiment, the support assembly 300 includes support 302 and fastening mechanism 304 as well as a sleeve 305 that serves as a liner for the framework 306 of the support 302. The support 302 and the framework 306 are generally the same structurally as the support 202 and framework 206 discussed supra with regard to the second preferred embodiment and FIGS. 18-22, and in the interests of brevity, the similarities are not repeated. The support 302 and framework 306 differ from the support 202 and framework 206 of FIGS. 18-22 in that the strut component 312 of each hinge mechanism 308,310 generally is not coplanar with the first and second strap interface components 330,332. In the support 302, the strut component 312 of each hinge mechanism 308,310 and the first and second strap interface components 330,332 are located on opposite sides of the arm components 314,316 of the hinge mechanisms 308,310. In this respect, the support 302 is structurally the same as the support 100.

The fastening mechanism 304 is structurally the same as the fastening mechanism 204 and includes four straps 352, 354,356,358. Each of the straps includes opposite ends having Velcro fasteners arranged such that each end may be passed through a respective opening 334 formed in the strap interface components 330,332 and folded back and attached to itself.

A Fourth Embodiment

Turning now to FIGS. 28-39, a support assembly 400 in accordance with a fourth embodiment of the invention is disclosed.

Figure 28:
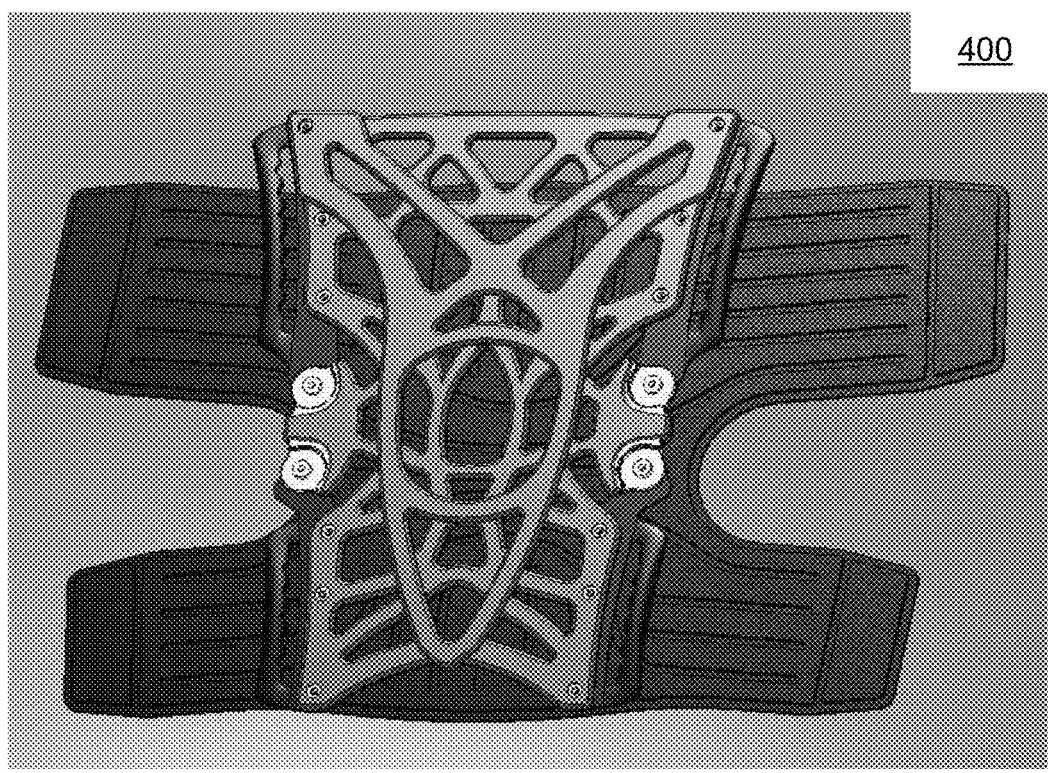
FIG. 28 is a perspective view of a support assembly 400 in accordance with another embodiment of the invention.
Figures 29, 30, 31:
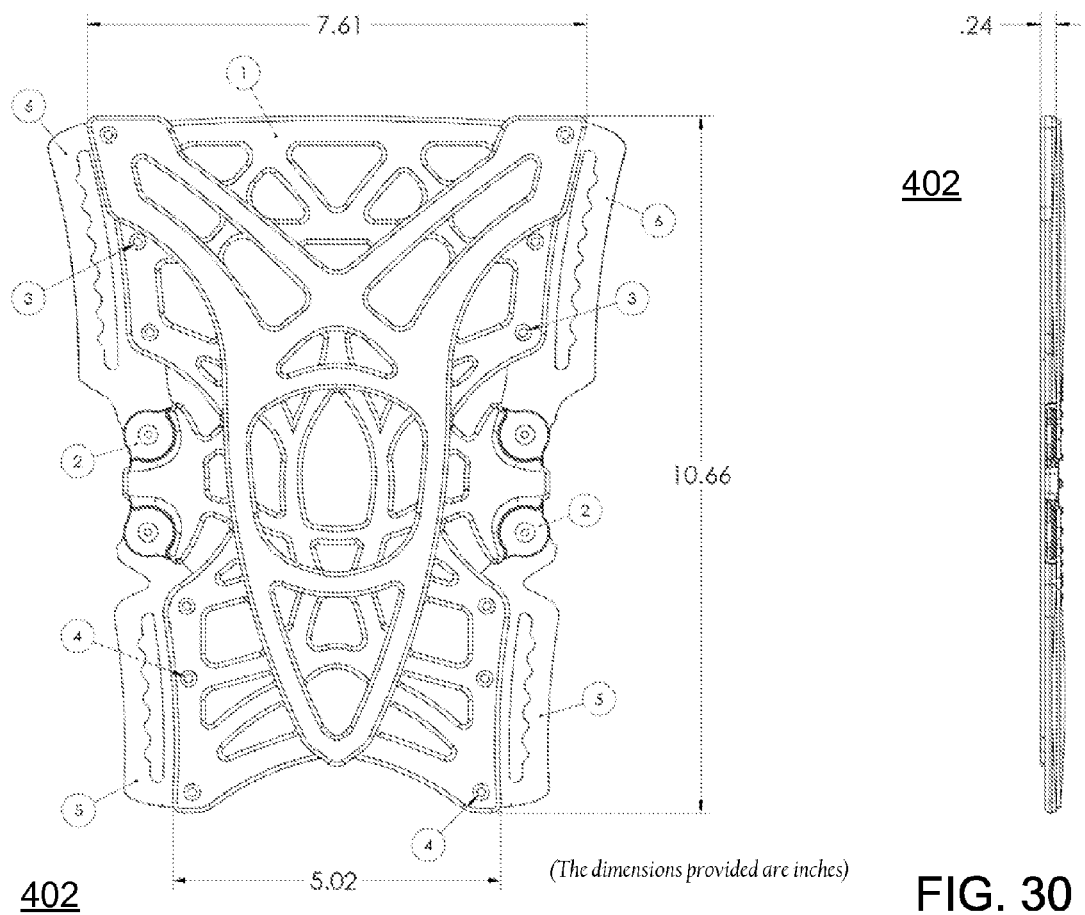
FIG. 29 is a plan view of a front of the support 402 of the support assembly 400 of FIG. 28.
FIG. 30 is a side plan view of the support 402 of FIG. 29.
FIG. 31 is a table of six different parts that are used in the support 402 of FIG. 29 as identified in FIG. 29 and as further identified in FIG. 33.
Figure 32:
FIG. 32 is a shaded plan view of the front of the support 402 of FIG. 29.
Figure 33:
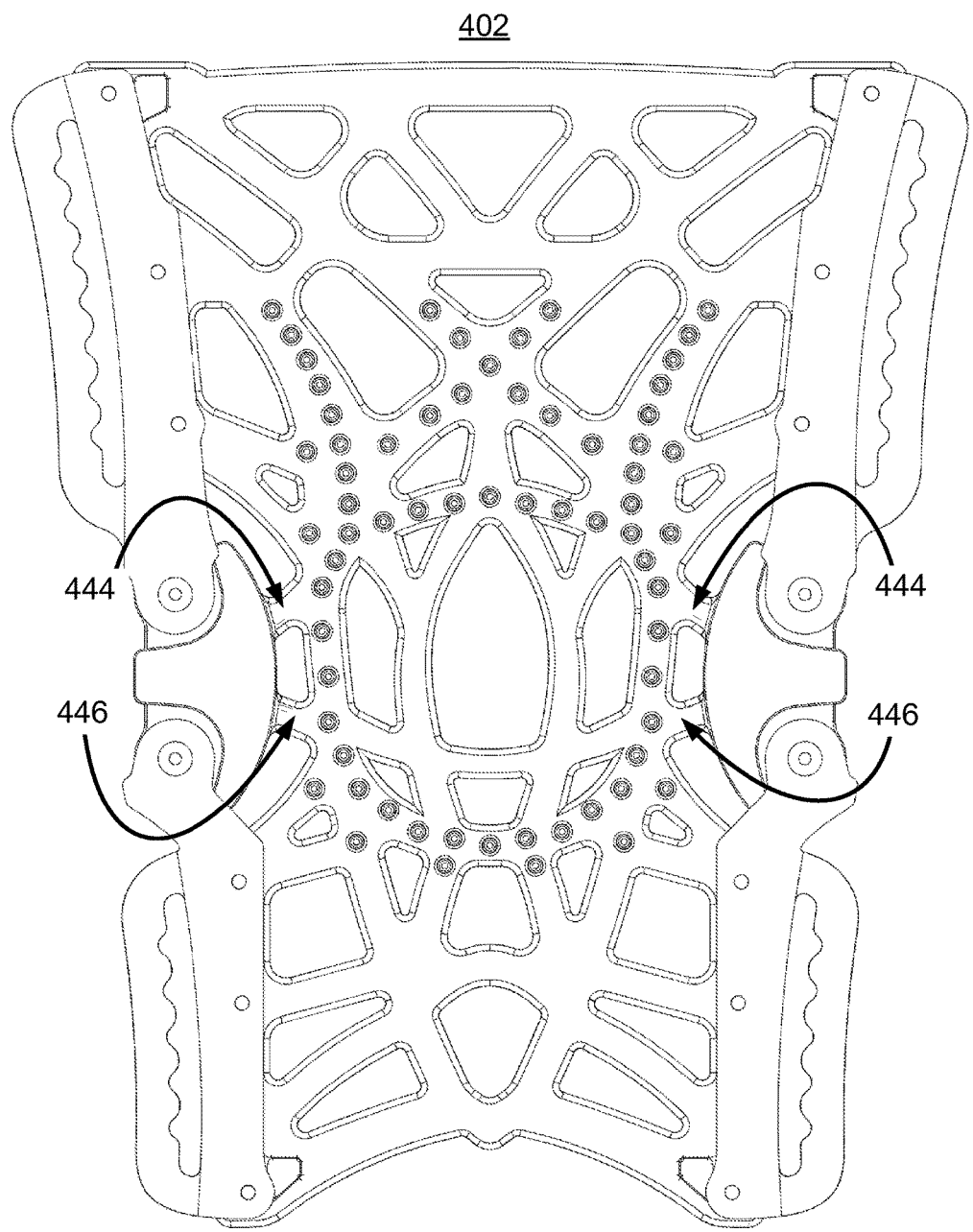
FIG. 33 is a plan view of the front of the support 402 of FIG. 29.
Figure 33B:
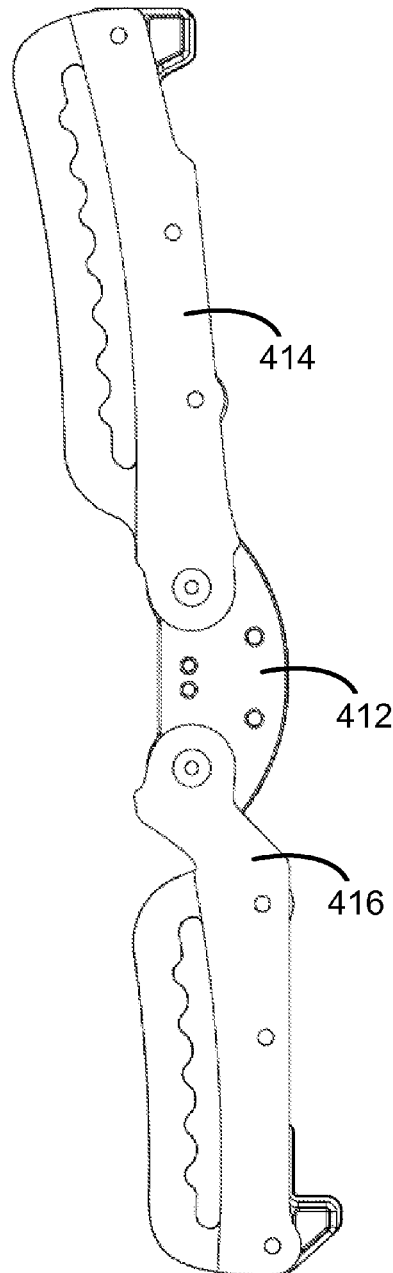
FIG. 33b is a plan view of the front of the hinge mechanisms of the support 402 of FIG. 29.
Figure 33B:
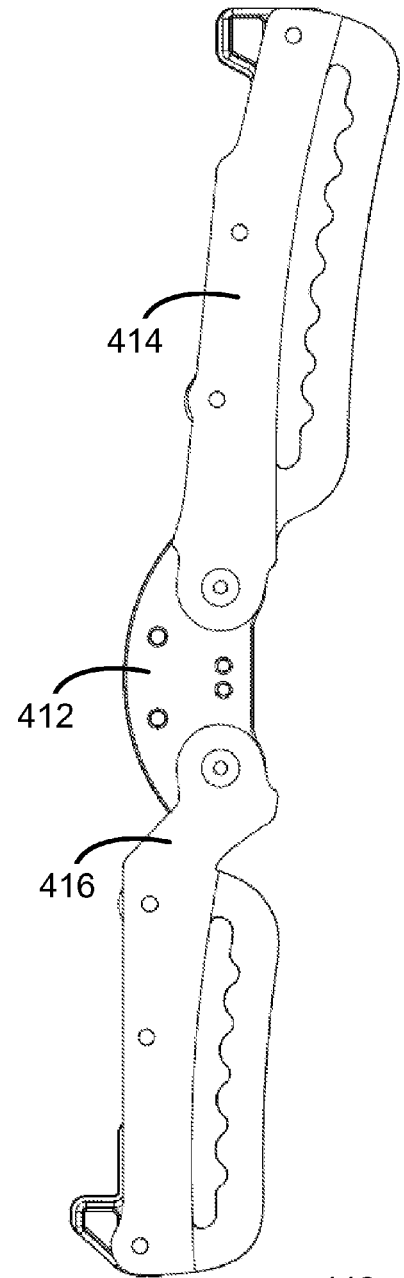
Figure 33C:
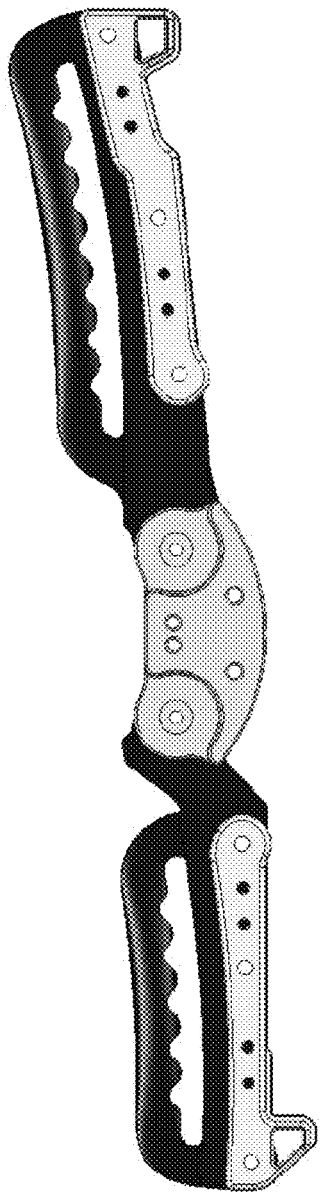
FIG. 33c is a shaded, plan view of the rear of the hinge mechanisms of the support 402 of FIG. 29.
Figure 33C:
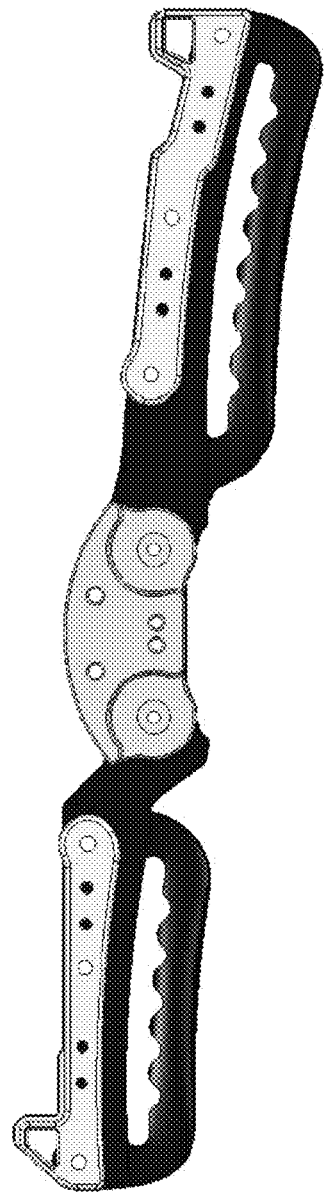
Figure 34:
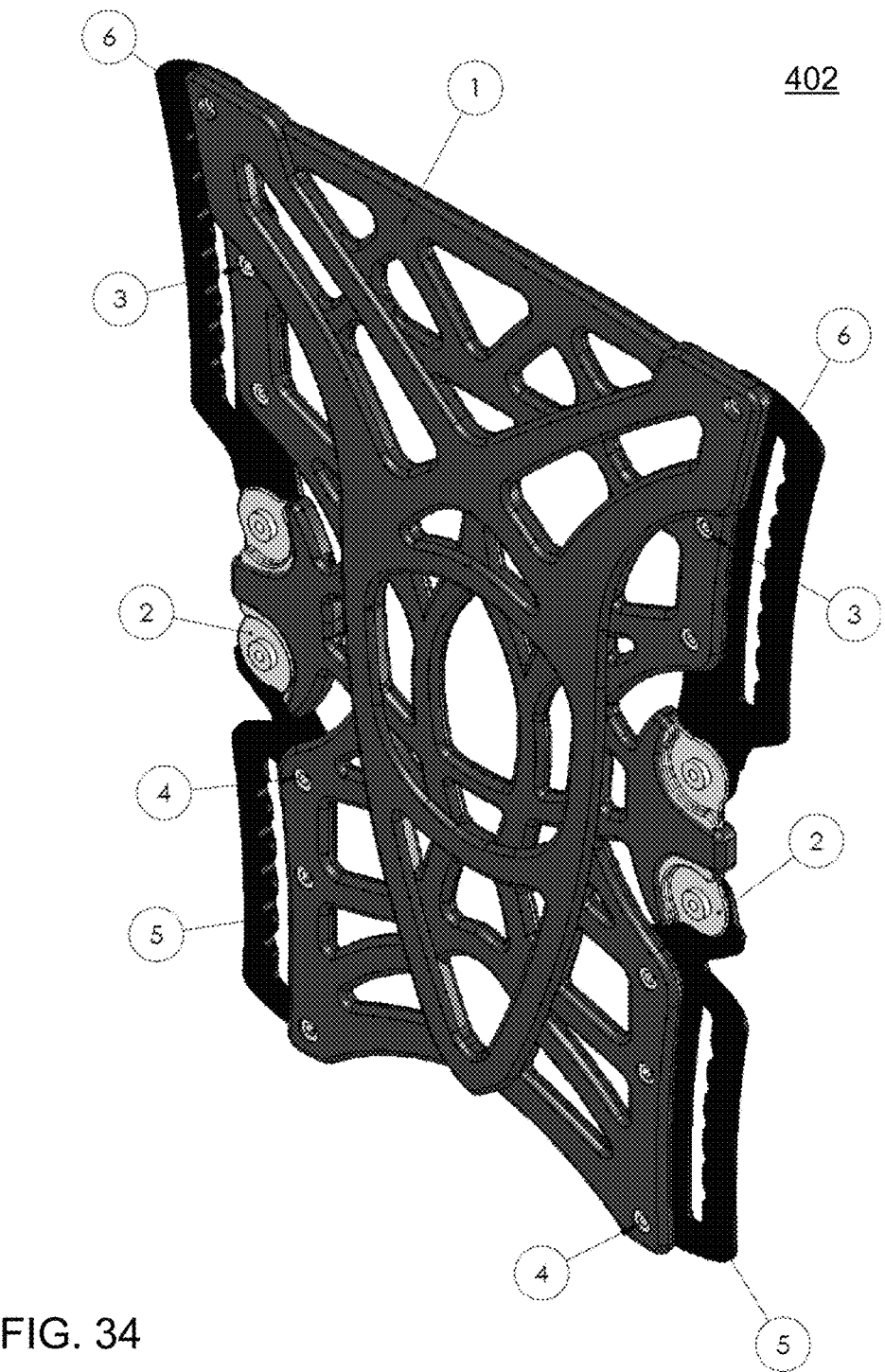
FIG. 34 is a shaded, perspective side view of the front of the support 402 of FIG. 29.
Figure 35:
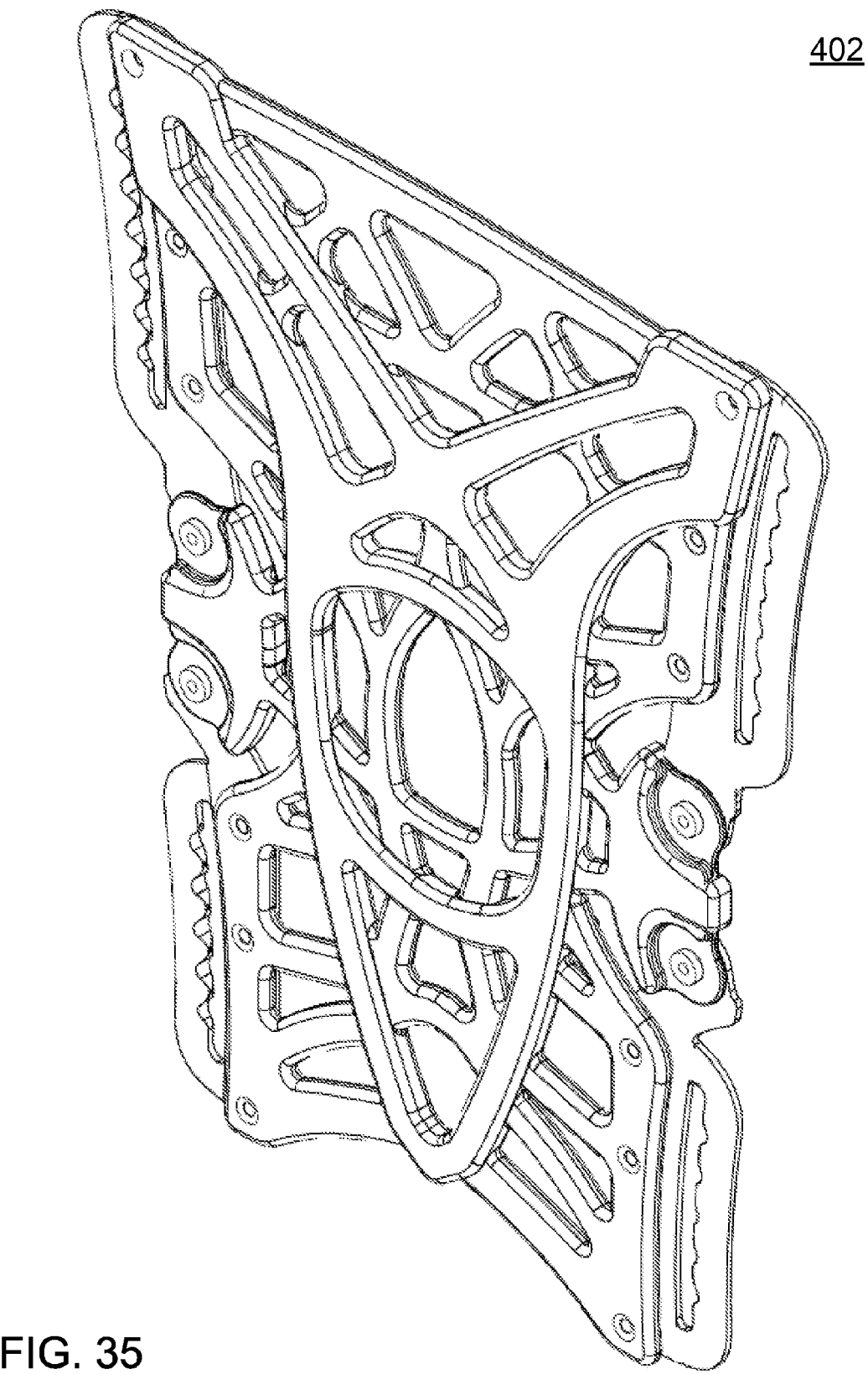
FIG. 35 is a perspective side view of the front of the support 402 of FIG. 29.
Figure 36:
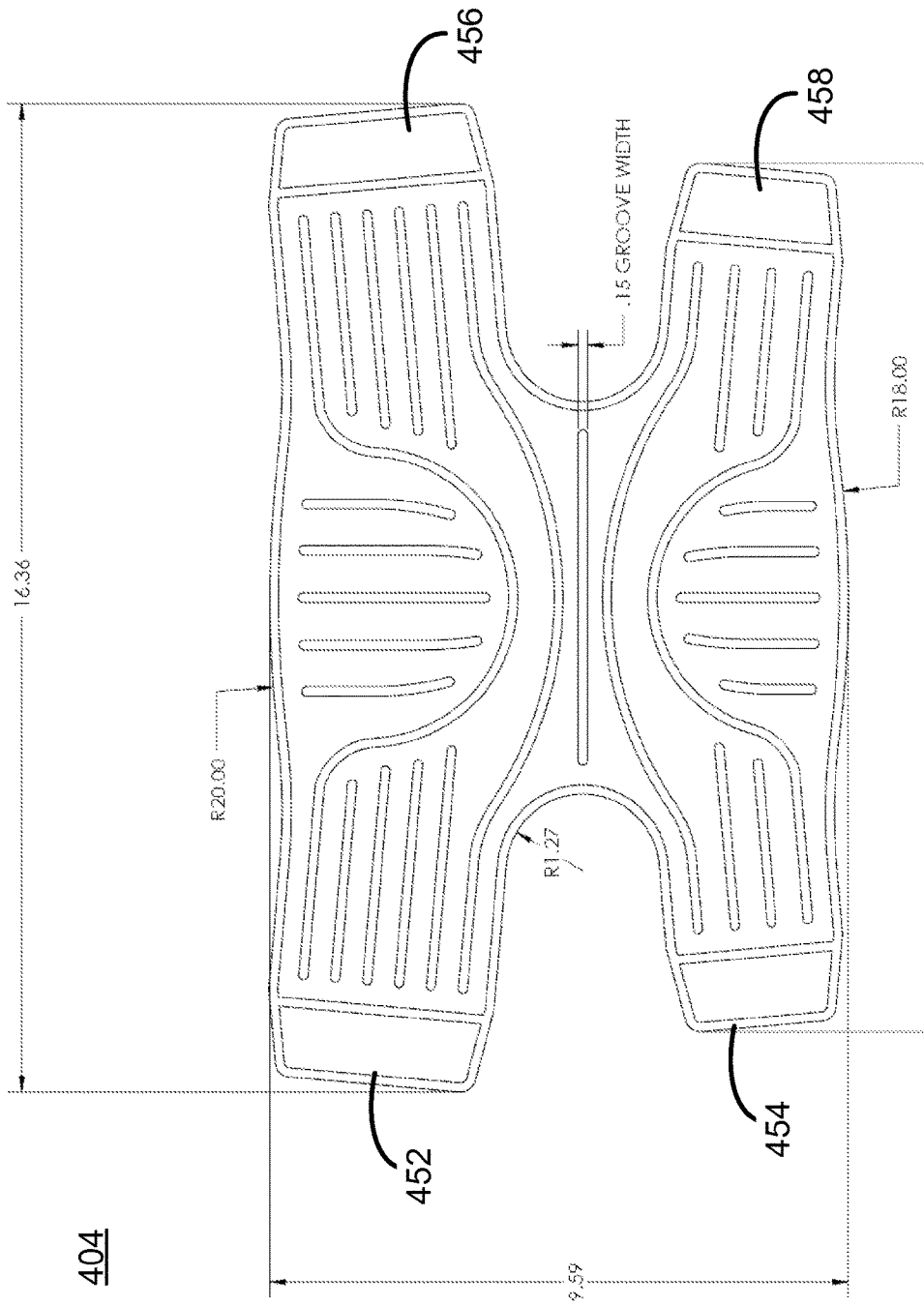
FIG. 36 is a plan view of a front of a fastening mechanism 404 of the support 400 of FIG. 28.
Figure 37:
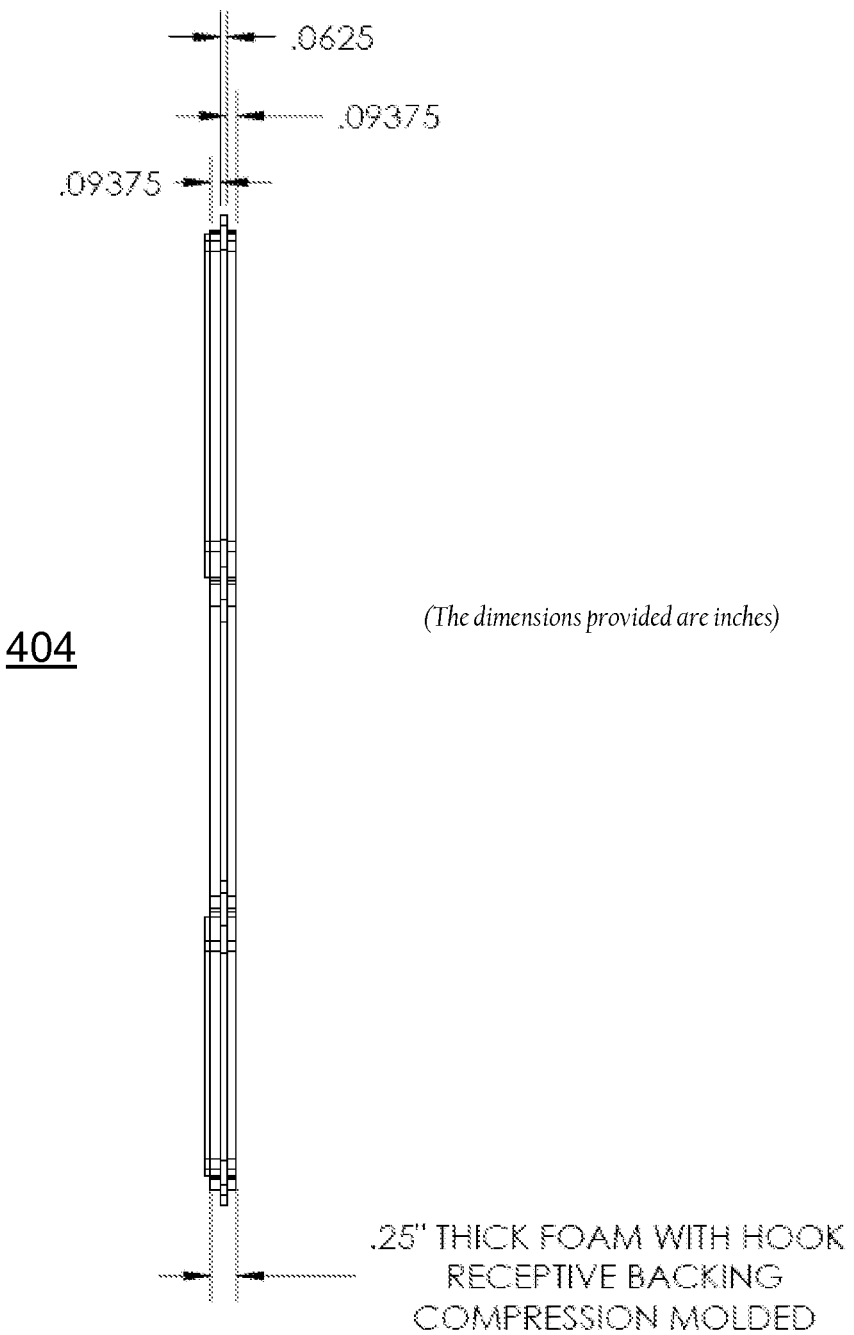
FIG. 37 is a side view of the fastening mechanism 404 of FIG. 36.
Figure 38:
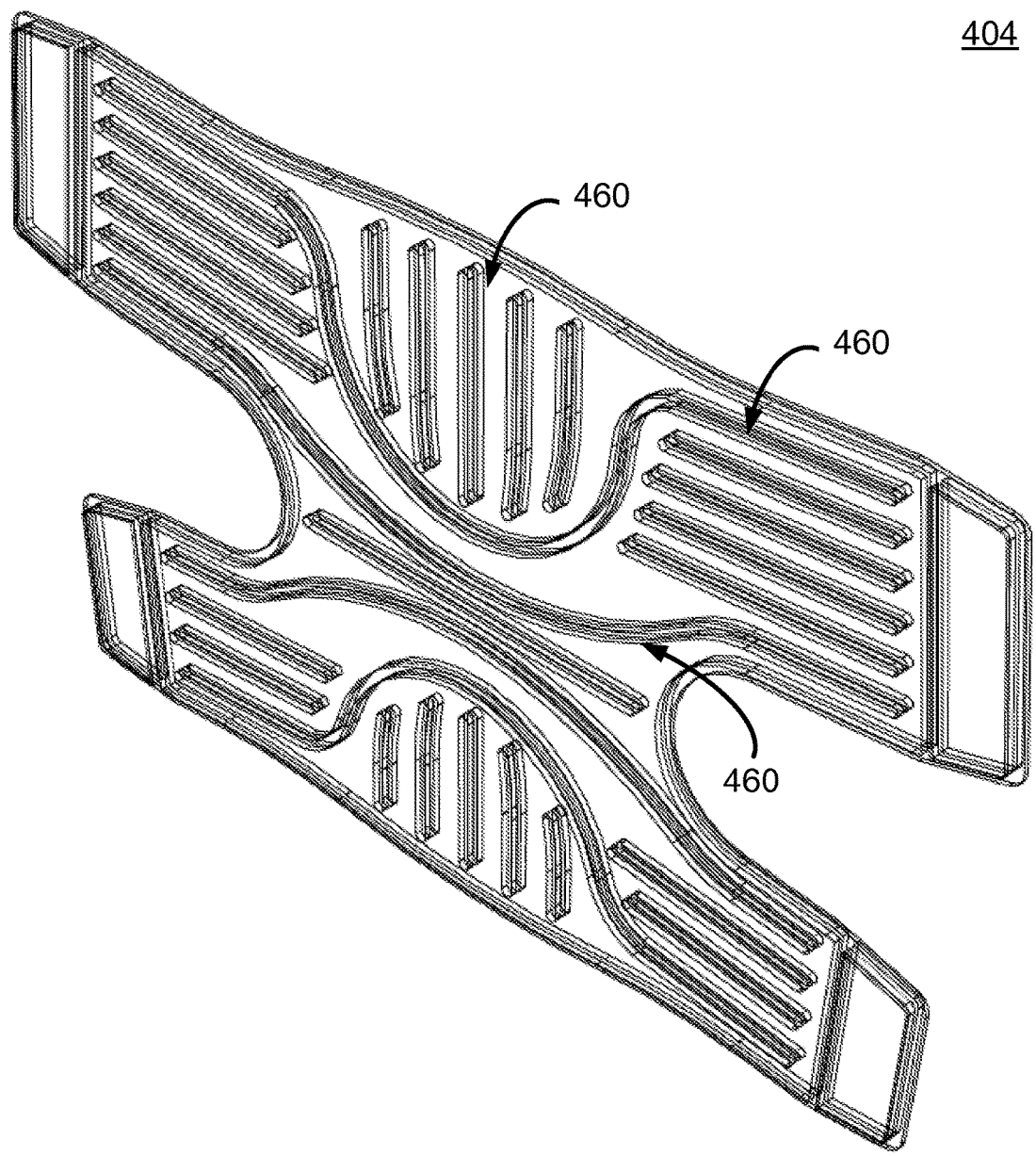
FIG. 38 is a perspective view of the front of the fastening mechanism 404 of FIG. 36.
Figure 39:
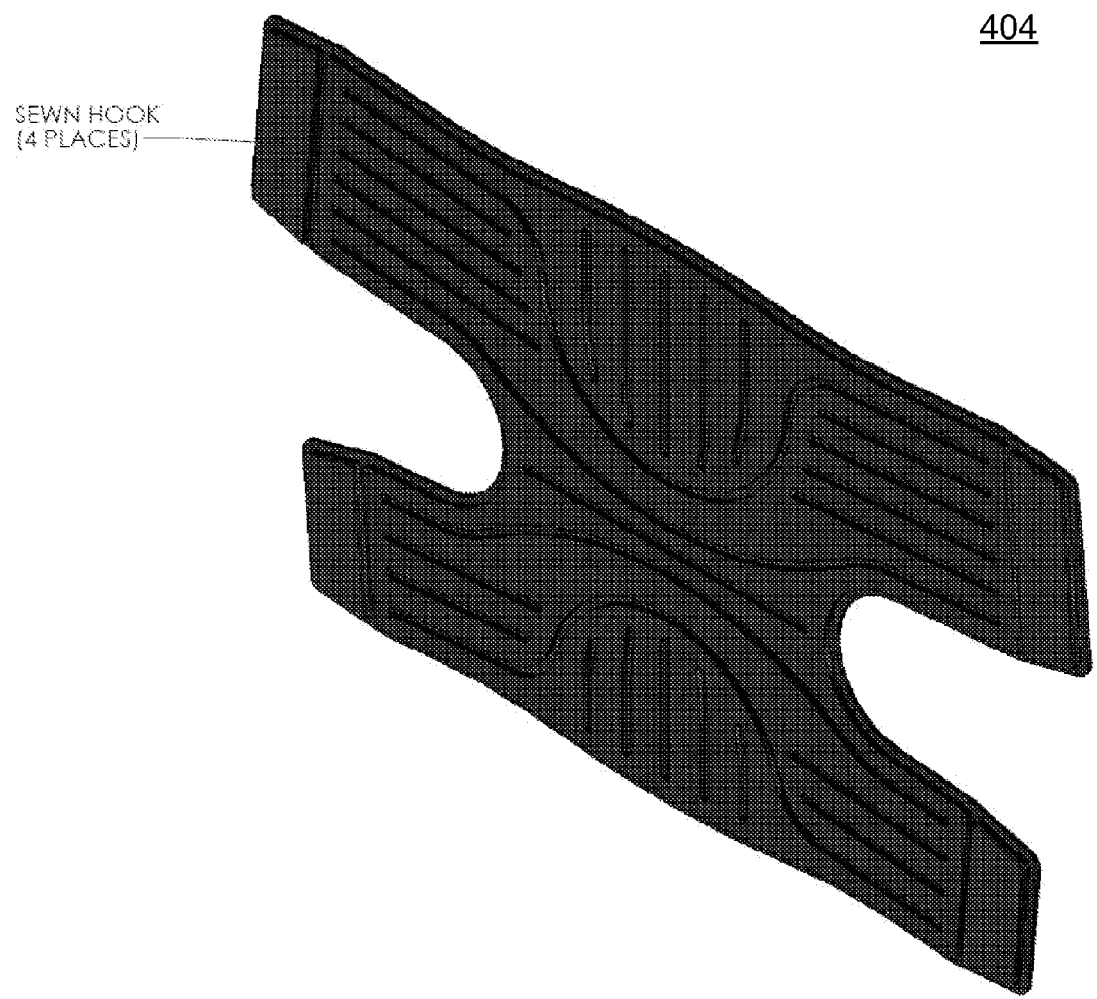
FIG. 39 is a shaded, perspective view of the front of the fastening mechanism 404 of FIG. 36.

In this regard, FIG. 28 is a perspective view of the support assembly 400; FIG. 29 is a plan view of a front of the support 402 of the support assembly 400; FIG. 30 is a side plan view of the support 402; FIG. 31 is a table of six different parts that are used in the support 402 as identified in FIG. 29 and as further identified in FIG. 33; FIG. 32 is a shaded plan view of the front of the support 402; FIG. 33 is a plan view of the front of the support 402; FIG. 34 is a shaded, perspective side view of the front of the support 402; FIG. 35 is a perspective side view of the front of the support 402; FIG. 36 is a plan view of a front of a fastening component 404 of the support 400; FIG. 37 is a side view of the fastening component 404; FIG. 38 is a perspective view of the front of the fastening component 404; and FIG. 39 is a shaded, perspective view of the front of the fastening component 404.

With regard to the support assembly 400 of the fourth embodiment, the support assembly 400 includes a support 402 that is generally the same structurally as the support 202 and framework 206 discussed supra with regard to the second preferred embodiment and FIGS. 18-22, and in the interests of brevity, the similarities are not repeated.

Figure 33D:
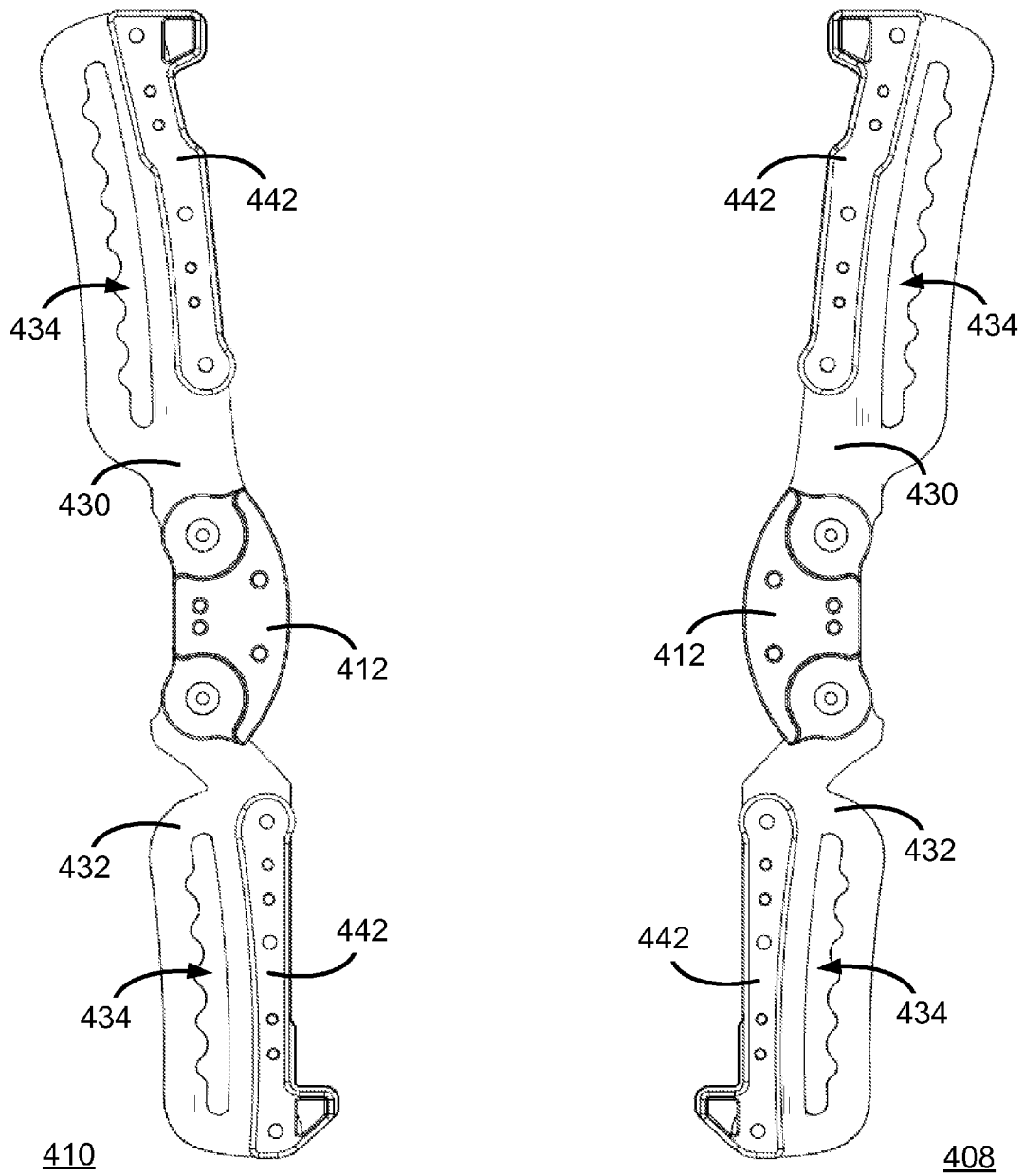
FIG. 33d is a plan view of the rear of the hinge mechanisms of the support 402 of FIG. 29.

The support 402 differs from the support 202 of FIGS. 18-22 in that the interconnected members defining the framework 406 extend across what otherwise would be the alignment opening of the framework 406. The shape and configuration of the arm components 414,416 (as perhaps best shown in FIGS. 33-33d) also differ somewhat from the shape and configuration of the arm components 214,216, although the structure and function remain the same.

Differences further include that only a single strap opening 434 is defined in each strap interface component 430,432 and that each such opening 434 includes ridges or teeth 440 for frictionally engaging one or more straps that extend therethrough. Moreover, while each hinge mechanism 408, 410 (best shown alone in FIGS. 33a-33d) includes the same components 412,414,416 as in the hinge mechanisms 208, 210, each hinge mechanism 408,410 of the support 402 further includes reinforcing members 442 that are affixed, by way of a plurality of rivets, to the strap interface components 430,432 for reinforcing these components against tension of fastening straps used to fasten the support 402 to the area of a knee. The same rivets further preferably affix the strap interface components 420,423 and the arm components 414,416 to the framework 406.

Yet another difference is the direct attachment of the strut component 412 of each hinge mechanism 408,410 to the framework 406 only by a limited number of interconnected members of the framework 406 and, as shown, only by two such interconnected members 444,446. In this respect, no interconnected member of the framework 406 directly bridges and connects together the strut component and either of the strap interface components 430,432. The fastening mechanism 404 of the support assembly 400 comprises a compression molded pad as illustrated in FIGS. 36-39 and itself serves as a liner for the framework 406 of the support 402 in abutting an area of the body including the knee joint. Due to the compression molding, the fastening mechanism includes raised areas defining ventilation channels 460 for engagement with the area of the body including the hinge joint. The fastening mechanism 404 includes four strap portions 452,454,456,458, the opposite ends of which include Velcro fasteners arranged such that each end may be passed through a respective opening 434 formed in the strap interface components 430,432 and folded back upon and attached to itself.

A Fifth Embodiment

Turning now to FIGS. 40-47, a support assembly 500 in accordance with a fifth embodiment of the invention is disclosed.

Figure 40:
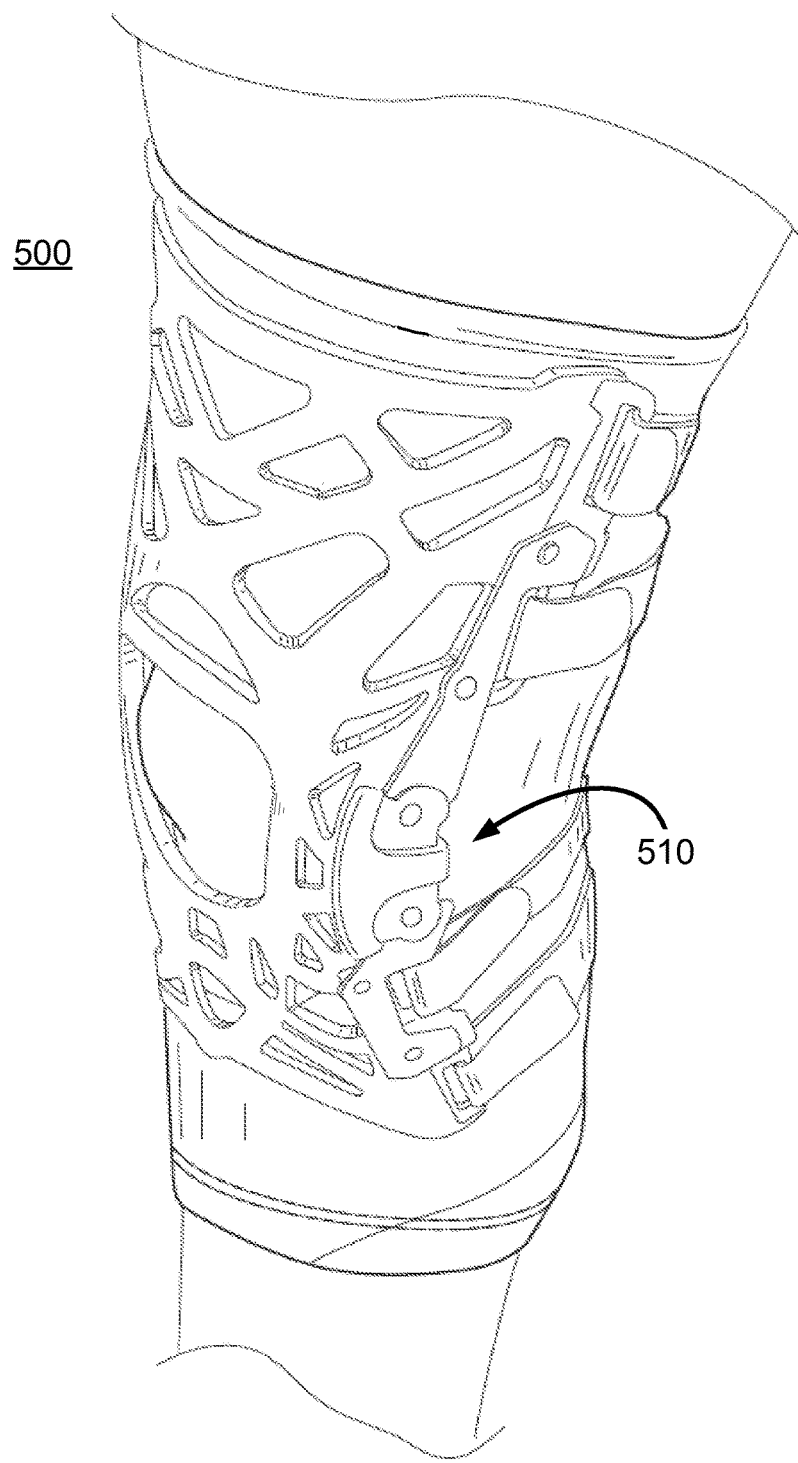
FIG. 40 is a side perspective view of another support assembly 500 being worn in accordance with an embodiment of the invention.
Figure 41:
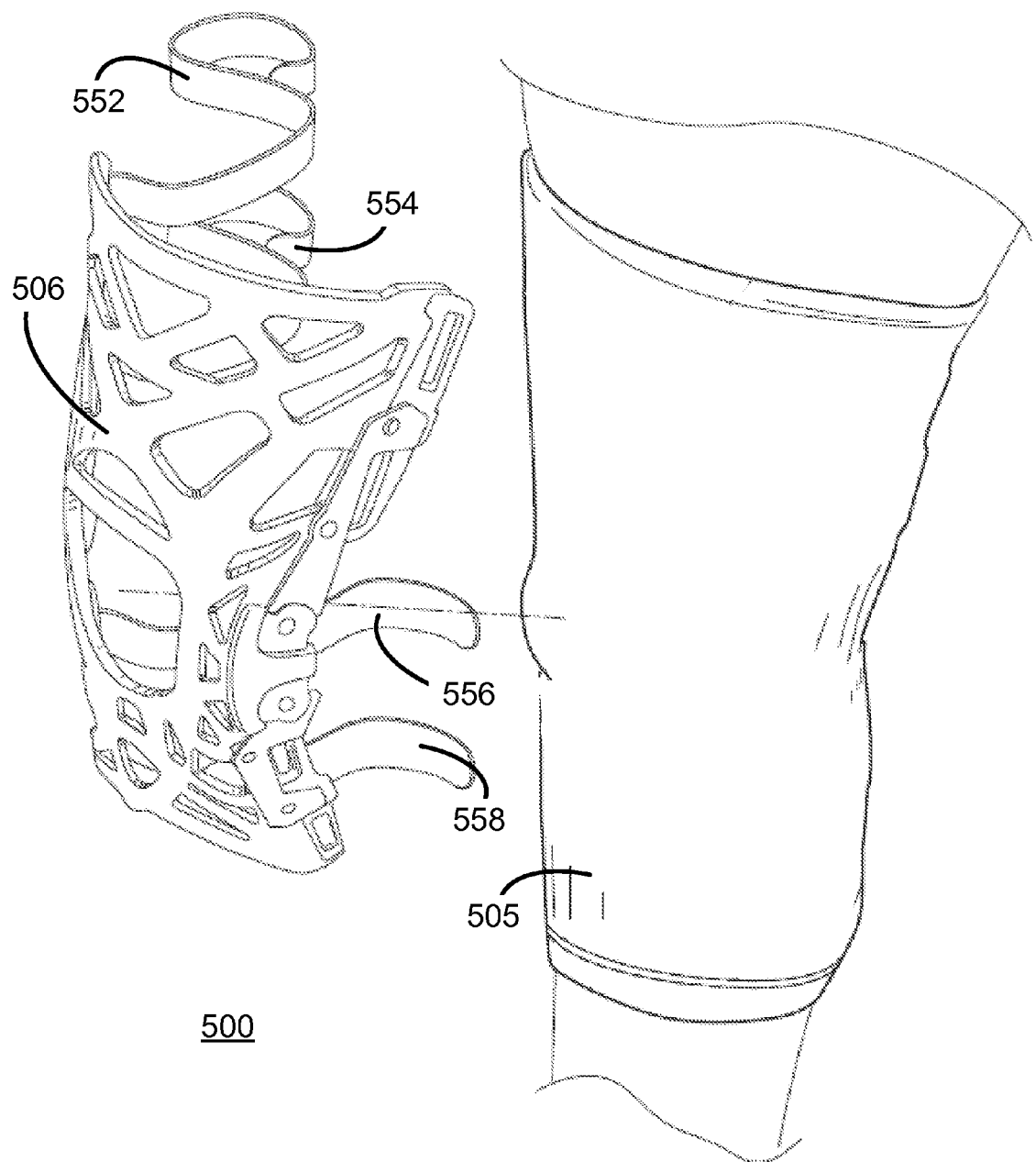
FIG. 41 is a side perspective view of a step in the detachment of the support assembly 500 of FIG. 40 from the area of a knee, in accordance with an embodiment of the invention.
Figure 42:
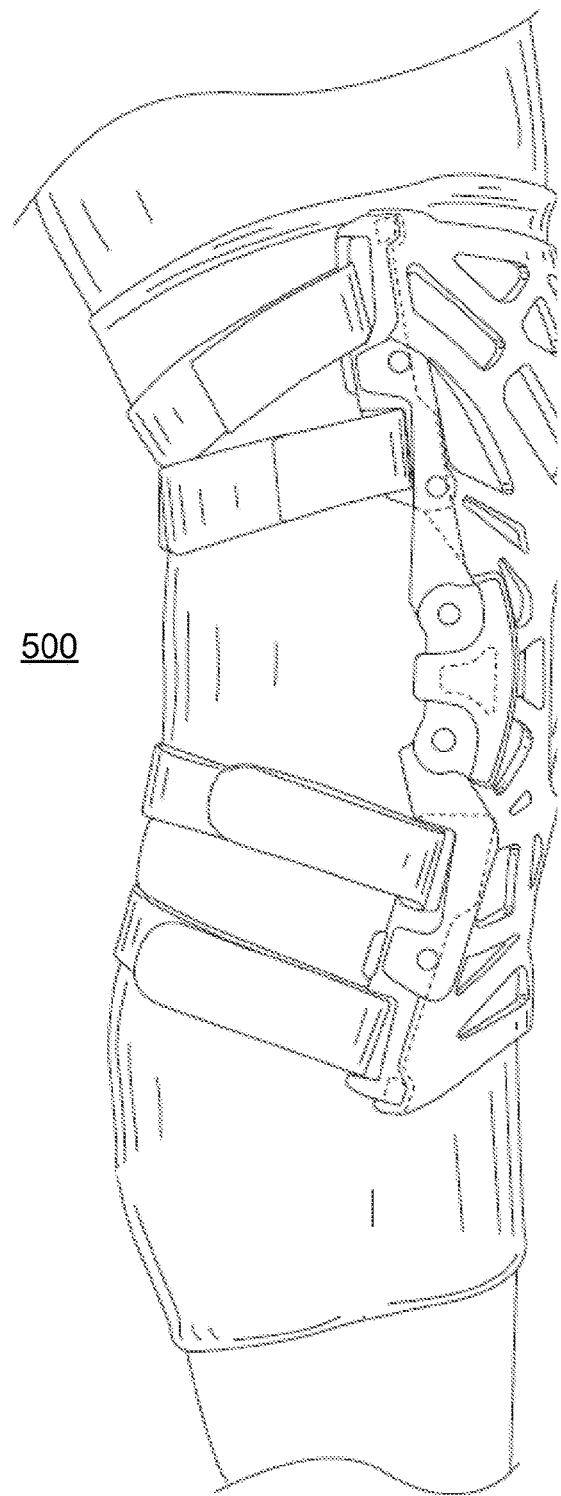
FIG. 42 is a perspective view of a back side of the support assembly 500 of FIG. 40 being worn in accordance with an embodiment of the invention.
Figure 43:
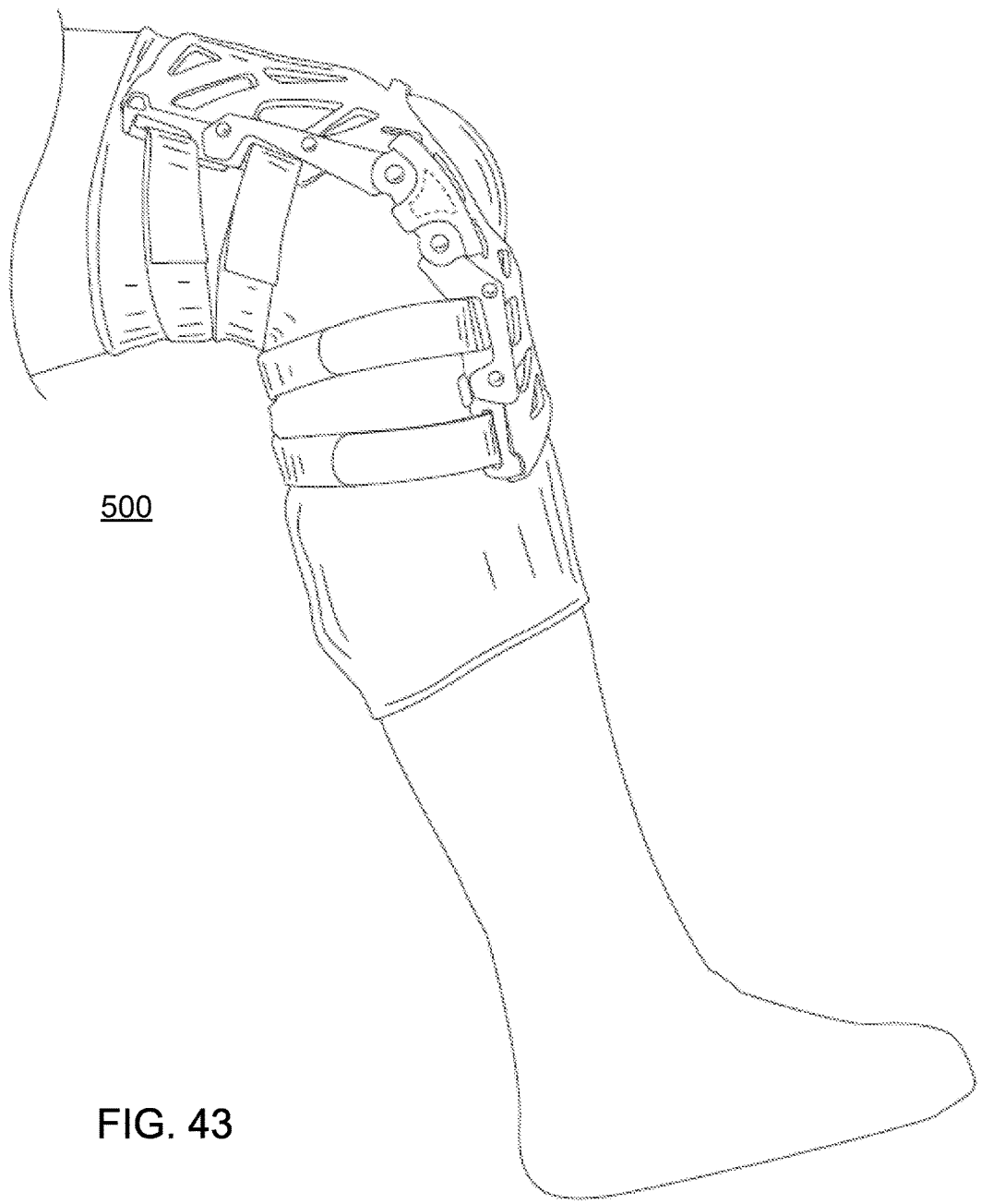
FIG. 43 is a side perspective view of the support assembly 500 of FIG. 40 in a first position.
Figure 44:
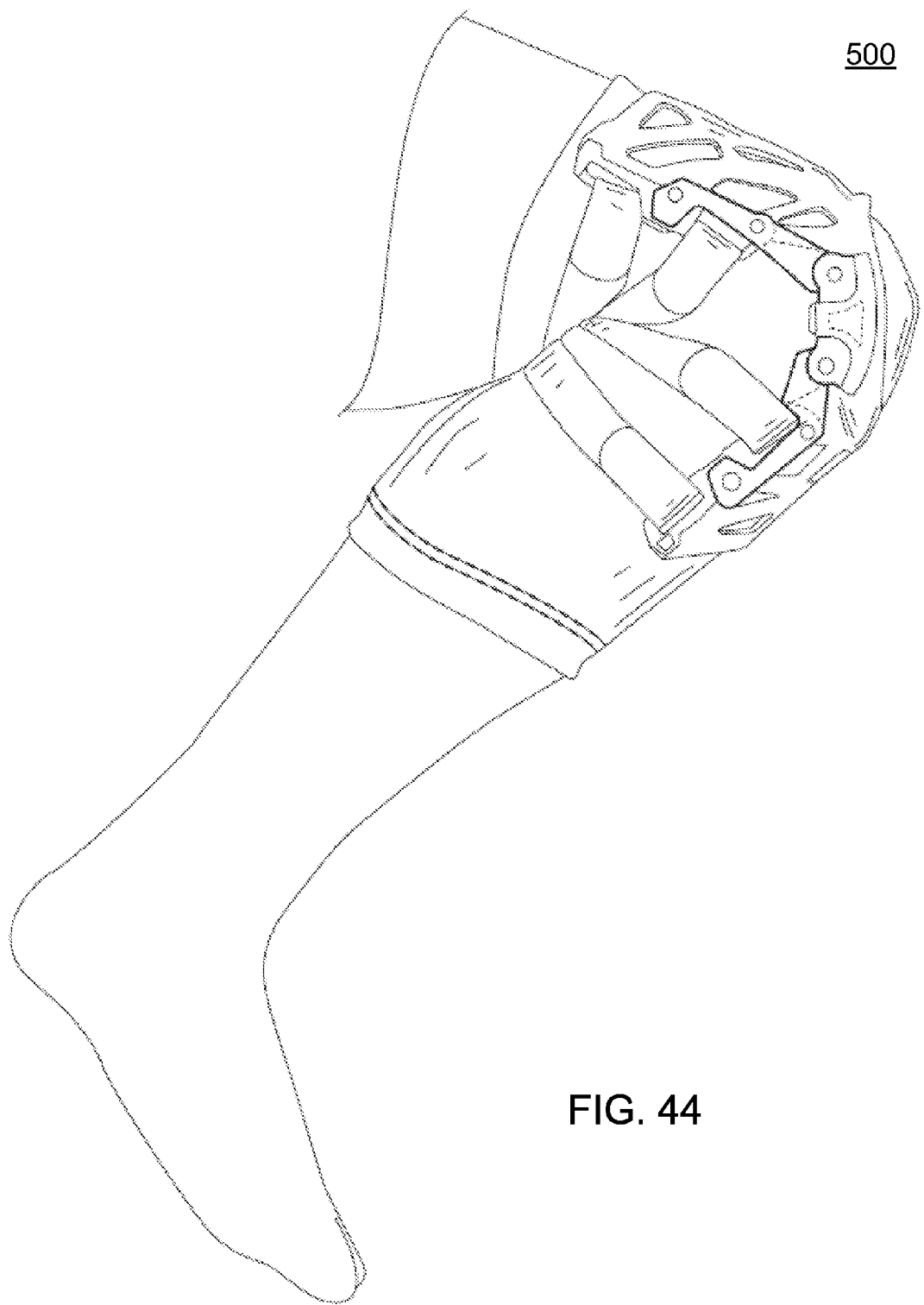
FIG. 44 is a side perspective view of the support assembly 500 of FIG. 40 in a second position in which the knee is further flexed (i.e., bent) relative to the first position of FIG. 43.
Figure 45:
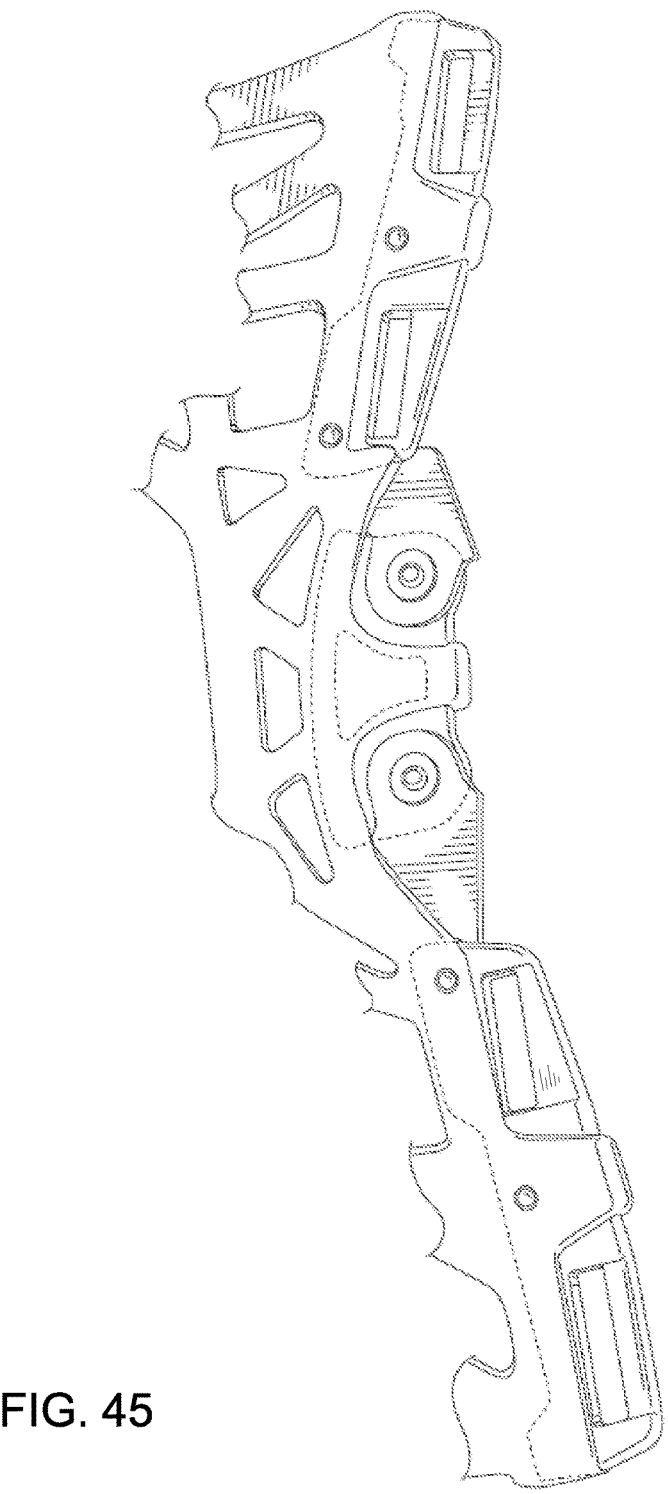
FIG. 45 is a partial, rear perspective view of the support assembly 500 of FIG. 40 that particularly shows a hinge mechanism of the support 502.
Figure 46:
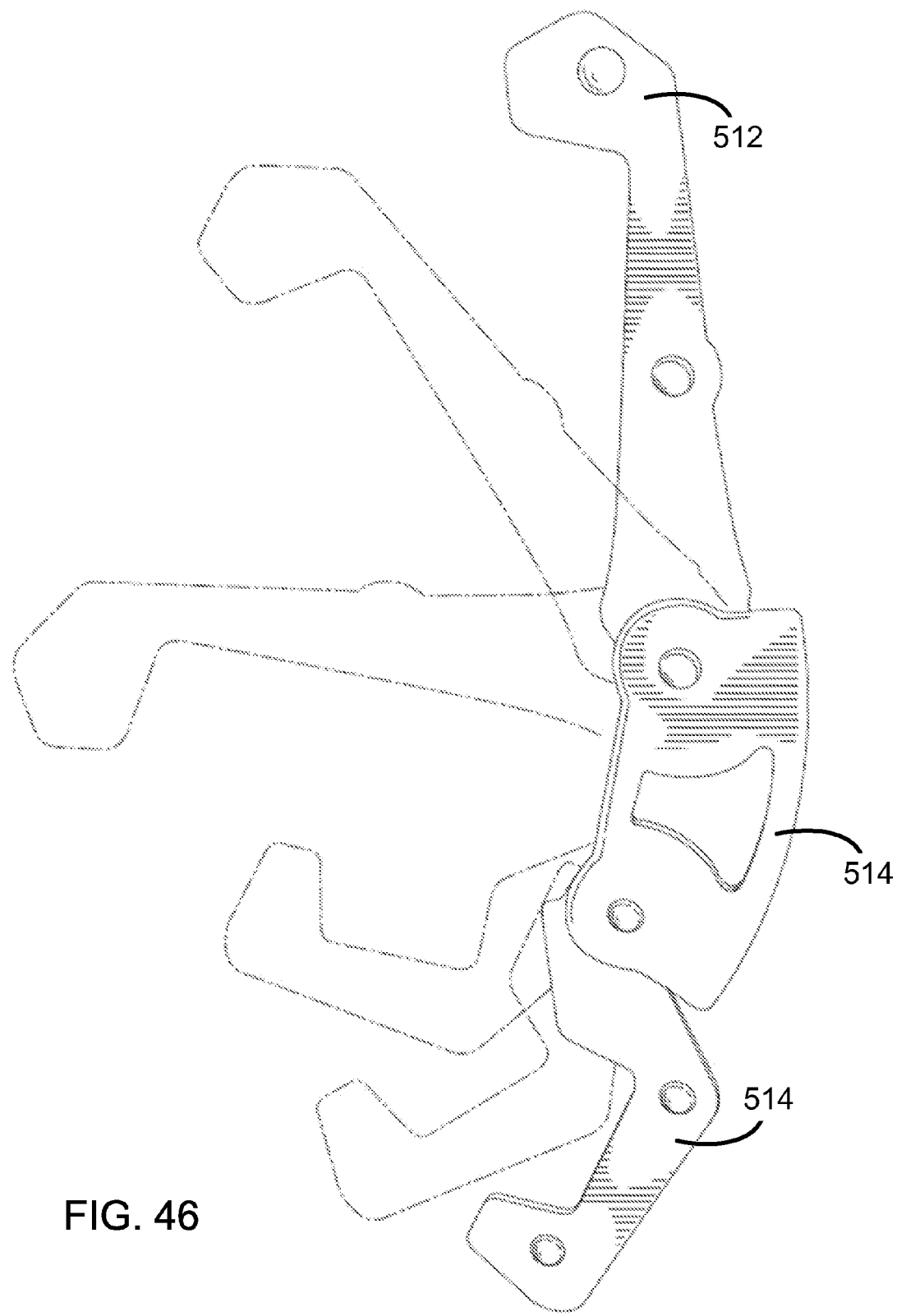
FIG. 46 is a schematic illustration, as seen from a rear view, of various positions of the hinge mechanism shown in FIG. 45.
Figure 47:
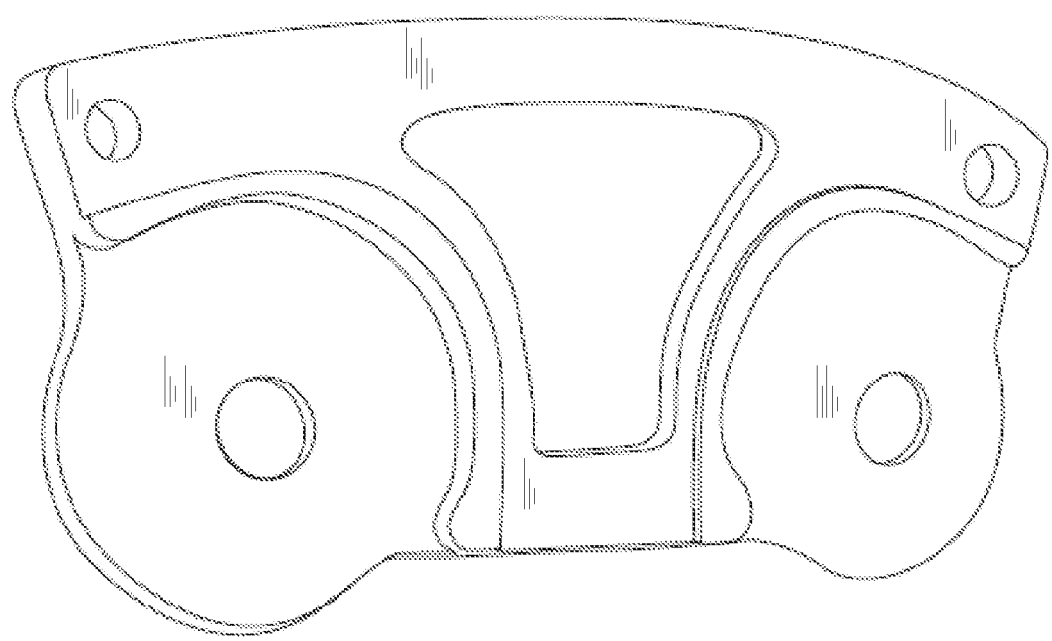
FIG. 47 is a perspective view of a front of a middle portion of the hinge mechanism of FIG. 45.

In this regard, FIG. 40 is a side perspective view of another support assembly 500 being worn in accordance with an embodiment of the invention; FIG. 41 is a side perspective view of a step in the detachment of the support assembly 500 from the area of a knee in accordance with an embodiment of the invention; FIG. 42 is a perspective view of a back side of the support assembly 500 being worn in accordance with an embodiment of the invention; FIG. 43 is a side perspective view of the support assembly 500 in a first position; FIG. 44 is a side perspective view of the support assembly 500 in a second position in which the knee is further flexed (i.e., bent) relative to the first position of FIG. 43; FIG. 45 is a partial, rear perspective view of the support assembly 500 that particularly shows a hinge mechanism of the support 502; FIG. 46 is a schematic illustration, as seen from a rear view, of various positions of the hinge mechanism shown in FIG. 45; and FIG. 47 is a perspective view of a front of a middle portion of the hinge mechanism of FIG. 45.

The support assembly 500 is structurally the same as the support assembly 300 discussed supra with regard to FIGS. 23-27, with the exception that the support 502 represents the support 302 turned inside-out and any protuberances on the inside surface of the support 302 have been omitted and/or provided on the inside surface of the support 502.

Preferred Manufacturing Methods

The supports of the invention and, in particular, the embodiments collectively shown and described above preferably are manufactured in injection molding processes, whereby the various components of each embodiment of the support, including, inter alia, the framework and strut components, are integrally formed from elastomeric materials. The injection molding processes preferably comprise, for each support, multi-step injection molding, whereby each component can be formed from different elastomeric materials having different elastic stretchability even though the components are integrally constructed.

In particular, the strut components and strap interface components can be formed through injection molding of a first elastomeric material, and then the framework can be formed through injection molding of a second elastomeric material about the strut components and strap interface components. This is particularly useful in manufacturing embodiments having strut components and strap interface components that are intended to provide a degree of rigidity to side areas of the framework, which can be readily made in an efficient and cost effective manner.

Additionally, the framework may be made of differing elastomeric materials and/or selected groups of interconnected segments of the framework can be made with varying thickness thereby providing different elastic characteristics and, thereby, providing different resistances to stretching in such areas.

CONCLUSIONS

While the foregoing supports in accordance with preferred embodiments of the invention relate to potentiating supports for the area of the body including the knee, other supports within the scope of the invention are similarly designed but are intended for use in, and are configured for, the area of the elbow. Other supports of the invention may include clothing having the expandable and recoverable frameworks with the hinging mechanisms as disclosed and discussed supra.

The supports of the drawings are useful for injury treatment or prevention, rehabilitation, and motion enhancement. For example, these potentiating supports for the knee provide a secure fitting and comfortable knee brace for the purposes of supporting knee alignment, comfort, and protection in the activities of daily living, athletics, and working and in the treatment or rehabilitation of an injured or ailing knee, all the while providing joint motion assistance for performance enhancement in everyday and athletic activities. In this regard, potential energy is stored and returned for use to assist the body in its natural knee movement in a preferred knee support of the present invention.

Based on the foregoing description, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention.

Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof.

What is claimed is:

1. A support for an area of a body that includes a hinge joint, comprising:
   (a) a hinge mechanism comprising an injection molded strut component and injection molded first and second arm components;
   (b) an elastically stretchable framework injection molded about the strut and arm components of the hinge mechanism, the framework being configured to extend across the hinge joint of the area of the body, and the framework defining a flexible, elastically stretchable web of elastomeric interconnecting members;
   (c) wherein the first arm component is connected to the strut component such that the first arm component is rotatable relative to the strut component only about a first pivot axis;
   (d) wherein the second arm component is connected to the strut component such that the second arm component is rotatable relative to the strut component only about a second pivot axis; and
   (e) wherein the strut component is configured to extend with the framework across the hinge joint such that the first pivot axis is located on a first side of the hinge joint and the second pivot axis is located on a second, opposite side of the hinge joint.

2. The support of claim 1, where the hinge mechanism is located along a first side edge of the framework, and wherein the support further comprises a second, identical hinge mechanism affixed to the framework and located along a second, opposite side edge of the framework, the strut component of the second hinge mechanism being configured to extend with the framework across the hinge joint such that the first pivot axis of the second hinge mechanism is located on the first side of the hinge joint and the second pivot axis of the second hinge mechanism is located on the second side of the hinge joint.

3. The support of claim 1, wherein the flexible framework is configured to be stretched and tensioned into abutment with the area of the body such that the flexible framework conforms to the shape and contour of the area of the body when stretched and tensioned, the flexible framework having a relaxed state when not stretched and tensioned in which the flexible framework does not conform to the shape and contour of the area of the body.

4. The support of claim 1, wherein the framework is in a first configuration when the hinge mechanism is in a first position, and the framework is in a second configuration when the hinge mechanism is in a second position, the elastically stretchable framework storing potential energy that is released as kinetic energy upon transitioning of the hinge mechanism from the second position to the first position.

5. The support of claim 1, wherein the framework encompasses and completely encircles at least a middle portion of the strut component.

6. The support of claim 1, wherein a first hinging member connects the first arm component to the strut component, the first hinging member including a cylindrical portion in abutment with which the first arm component and strut component rotate, and wherein a second hinging member connects the second arm component to the strut component, the second hinging member including a cylindrical portion in abutment with which the second arm component and strut component rotate, the first axis extending through the cylindrical portion of the first hinging member and the second axis extending through the cylindrical portion of the second hinging member.

7. The support of claim 1, further comprising first and second strap interface components, each strap interface component being affixed to the framework, the first strap interface component being connected to the first arm component and defining at least one opening therein configured to receive therethrough a strap for attachment of the framework to the body on the first side of the hinge joint, and the second strap interface component being connected to the second arm component and defining at least one opening therein configured to receive therethrough a strap for attachment of the framework to the body on the second side of the hinge joint.

8. The support of claim 7, wherein each of the first and second strap interface components are at least partially embedded in a material of the framework.

9. A support for an area of a body that includes a hinge joint, comprising:
(a) first and second hinge mechanisms;
(b) a flexible, elastically stretchable framework injection molded about the first and second hinge mechanisms, the framework comprising a web of elastomeric interconnecting members formed of a first elastomeric material, the web including an intermediate portion configured to extend across the hinge joint;
(c) wherein the framework is injection molded about the first hinge mechanism such that the first hinge mechanism is secured within the web proximate a first side of the intermediate portion of the web, the first hinge mechanism comprising an injection molded strut component formed of a second elastomeric material at least partially embedded in a material of the web and first and second injection molded arm components formed of the second elastomeric material at least partially embedded in the material of the web, the first and second arm components being connected to respective opposite end portions of the strut component such that the first and second arm components are rotatable relative to the strut component about respective pivot axes located at opposite end portions of the strut component; and
(d) wherein the framework is injection molded about the second hinge mechanism such that the first hinge mechanism is secured within the web proximate a second, opposite side of the intermediate portion of the web, the second hinge mechanism comprising an injection molded strut component formed of the second elastomeric material at least partially embedded in the material of the web and first and second injection molded arm components formed of the second elastomeric material at least partially embedded in the material of the web, the first and second arm components of the second hinge mechanism being connected to respective opposite end portions of the strut component of the second hinge mechanism such that the first and second arm components of the second hinge mechanism are rotatable relative to the strut component of the second hinge mechanism about respective pivot axes located at opposite end portions of the strut component of the second hinge mechanism;
(e) wherein each of the strut components and arm components of the first and second hinge mechanisms comprises components that are distinct from one another; and
(f) wherein the first elastomeric material is different from the second elastomeric material.

10. The support of claim 9, wherein the web encompasses and completely encircles at least a middle portion of the strut component.

11. The support of claim 9, further comprising strap interface components, each strap interface component being affixed to the web, the first strap interface component being connected to the first arm component and defining at least one opening therein configured to receive therethrough a strap for attachment of the web to the body on a first side of the hinge joint, and the second strap interface component being connected to the second arm component and defining at least one opening therein configured to receive therethrough a strap for attachment of the web to the body on the second side of the hinge joint.

12. The support of claim 11, wherein each of the strap interface components is at least partially embedded in the material of the web.

13. The support of claim 9, wherein each of the strut components and arm components of the first and second hinge mechanisms comprises a generally planar component.

14. A support for an area of a body that includes a hinge joint, comprising:
(a) a hinge mechanism comprising an injection molded strut component and injection molded first and second arm components;
(b) an elastically stretchable framework injection molded about the strut and arm components of the hinge mechanism, the framework being configured to extend across the hinge joint of the area of the body, and the framework defining a flexible, elastically stretchable web of elastomeric interconnecting members;
(c) wherein the first arm component is connected to the strut component such that the first arm component is rotatable relative to the strut component only about a first pivot axis;
(d) wherein the second arm component is connected to the strut component such that the second arm component is rotatable relative to the strut component only about a second pivot axis; and
(e) wherein the strut component is configured to extend with the framework across the hinge joint such that the first pivot axis is located on a first side of the hinge joint and the second pivot axis is located on a second, opposite side of the hinge joint;
(f) wherein the strut and arm components of the hinge mechanism are formed of a first elastomeric material, and the framework is formed of a second elastomeric material injection molded about the first elastomeric material, the second elastomeric material being different from the first elastomeric material.

15. The support of claim 14, where the hinge mechanism is located along a first side edge of the framework, and wherein the support further comprises a second, identical hinge mechanism affixed to the framework and located along a second, opposite side edge of the framework, the strut component of the second hinge mechanism being configured to extend with the framework across the hinge joint such that the first pivot axis of the second hinge mechanism is located on the first side of the hinge joint and the second pivot axis of the second hinge mechanism is located on the second side of the hinge joint.

16. The support of claim 14, wherein the flexible framework is configured to be stretched and tensioned into abutment with the area of the body such that the flexible framework conforms to the shape and contour of the area of the body when stretched and tensioned, the flexible framework having a relaxed state when not stretched and tensioned in which the flexible framework does not conform to the shape and contour of the area of the body.

17. The support of claim 14, wherein the framework is in a first configuration when the hinge mechanism is in a first position, and the framework is in a second configuration when the hinge mechanism is in a second position, the elastically stretchable framework storing potential energy that is released as kinetic energy upon transitioning of the hinge mechanism from the second position to the first position.

18. The support of claim 14, wherein the framework encompasses and completely encircles at least a middle portion of the strut component.

19. The support of claim 14, wherein a first hinging member connects the first arm component to the strut component, the first hinging member including a cylindrical portion in abutment with which the first arm component and strut component rotate, and wherein a second hinging member connects the second arm component to the strut component, the second hinging member including a cylindrical portion in abutment with which the second arm component and strut component rotate, the first axis extending through the cylindrical portion of the first hinging member and the second axis extending through the cylindrical portion of the second hinging member.

20. The support of claim 14, further comprising first and second strap interface components, each strap interface component being affixed to the framework, the first strap interface component being connected to the first arm component and defining at least one opening therein configured to receive therethrough a strap for attachment of the framework to the body on the first side of the hinge joint, and the second strap interface component being connected to the second arm component and defining at least one opening therein configured to receive therethrough a strap for attachment of the framework to the body on the second side of the hinge joint.

* * * * *